US007087224B2

(12) United States Patent
Kay et al.

(10) Patent No.: US 7,087,224 B2
(45) Date of Patent: Aug. 8, 2006

(54) METHOD OF TREATING ANEMIA BY ADMINISTERING IL-1RA

(75) Inventors: Jonathan Kay, Newton Centre, ME (US); Dorothy McCabe, Moorpark, CA (US); Richard Newmark, Newbury Park, CA (US); Marco A. Coccia, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 633 days.

(21) Appl. No.: 09/969,739

(22) Filed: Oct. 2, 2001

(65) Prior Publication Data

US 2002/0077294 A1 Jun. 20, 2002

Related U.S. Application Data

(60) Provisional application No. 60/244,792, filed on Oct. 31, 2000.

(51) Int. Cl.
*A61K 38/19* (2006.01)

(52) U.S. Cl. .............................. 424/85.1; 514/2; 514/8; 514/12

(58) Field of Classification Search .................... 514/2, 514/8, 12; 424/85.1, 85.2
See application file for complete search history.

(56) References Cited

U.S. PATENT DOCUMENTS 5,075,222 A    12/1991   Hannum et al.

FOREIGN PATENT DOCUMENTS

| EP | 0 393 438 | 4/1990 |
|----|-----------|--------|
| EP | 0 422 339 | 1/1998 |
| EP | 0 855 404 | 7/1998 |
| EP | 0 148 605 | 12/1998 |
| WO | WO 96/09323 | 3/1996 |
| WO | WO 97/28828 | 8/1997 |
| WO | WO 98/01555 | 1/1998 |
| WO | WO 00/24893 | 5/2000 |
| WO | WO 00/26209 | 5/2000 |
| WO | WO 00/59530 | 10/2000 |
| WO | WO 02/096461 | 12/2002 |

OTHER PUBLICATIONS

Thomas et al. Agents and Actions, (Sep. 1991) 34 (1–2), pp. 187–190.*
Carter et al. (1990), "Purification, cloning, expression and biological characterization of an interleukin–1 receptor antagonist protein," *Nature* 344:633–638.
Means et al. (1999), "Commentary: An anemia of chronic disease, after all?, " *J. Investigative Medicine* 47(5): 203.
Peeters et all. (1996), "Course and Characteristics of Anaemia in Patients with Rheumatoid Arthritis of Recent Onsent," *Ann. Rheum. Dis.*, 55: 162–68.
Pincus et al. (1990), "Multicenter Study of Recombinant Human Erythropoietin in Correction of Anemia in Rheumatoid Arthritis," *Am. J. Med.* 89:161.
Tanaka et al. (1999), "Autologous blood transfusion with recombinant erythropoietin treatment in anaemic patients with rheumatoid arthritis," *Clinical Rheumatology* 18(4): 293–298.
Voulgari, et al. (1999), "Role of Cytokines in the Pathogenesis of Anemia of Chronic Disease in Rheumatoid Arthritis," *Clin. Immunol.* 92:153–160.
Galon et al. (2000), "TNFRSF1A Mutations and Autoinflammatory Syndroms," *Current Opinion in Immunology* 12: 479–486.
Glennie et al. (2000), "Clinical Trials of Antibody Therapy," *Immunology Today* 21(8): 403–410.
Lee et al. (1999), "Erythropoietin plus iron supplement prevents significant anemia during concurrent chemo–radiation therapy in patients with locally–advanced inoperable non–small cell lung cancer," *Proceedings of the American Association for Cancer Research Annual Meeting* 40: 642.
MacDougall et al. (1999), "Pharmacokinetics of Novel Erythropoietin Stimulating Protein Compared with Epoietin Alfa in Dialysis Patients," *J. Am. Society of Nephrology* 10: 2392–2395.
Means (1999), "Advances in the Anemia of Chronic Disease," *International J. of Hematol.* 70(1):7–12.
Faquin et al. (1992), "Effect of Inflammatory Cytokines on Hypoxia–Induced Erythropoietin Production," *Blood* 79:1987–1994.
Means et al. (1992), "Progress in Understanding the Pathogenesis of the Anemia of Chronic Disease," *Blood* 80:1639–1647.
Nieken et al. (1995), "Recombinant Human Interleukin–6 Induces a Rapid and Reversible Anemia in Cancer Patients," *Blood* 86:900–905.
Smith et al. (1992), "Anaemia of chronic disease in rheumatoid arthritis: effect of the blunted response to erythropoietin and of interleukin 1 production by marrow macrophages," *Annals of the Rheumatic Diseases* 51: 753–757.
Sun et al. (1993), "The Influence of Recombinant Human Interleukin–6 on Blood and Immune Parameters in Middle–aged and Old Rhesus Monkeys," *Lymphokine Cytokine Research* 12:449–455.

* cited by examiner

*Primary Examiner*—Prema Mertz
(74) *Attorney, Agent, or Firm*—Timothy J. Gaul; Ron K. Levy; Stuart L. Watt

(57) ABSTRACT

The invention relates to methods of treating a blood disorder in a mammal with an interleukin-1 (IL-1) inhibitor. The invention also relates to methods of treating a blood disorder in a mammal with an IL-1 inhibitor, a TNF inhibitor and an erythropoietin (EPO) receptor agonist. The invention also relates to compositions of an IL-1 inhibitor and compositions of an IL-1 inhibitor, a TNF inhibitor and an EPO receptor agonist.

14 Claims, 23 Drawing Sheets

FIG. 1

Baseline Demographics and Disease History by Treatment Group

|  | Placebo (N = 121) | IL-1ra 30 mg (N = 119) | IL-1ra 75 mg (N = 116) | IL-1ra 150 mg (N = 116) | All (N = 351) |
|---|---|---|---|---|---|
| Sex – n (%) |  |  |  |  |  |
| Male | 36 (29.8) | 34 (28.6) | 24 (20.7) | 24 (20.7) | 82 (23.4) |
| Female | 85 (70.2) | 85 (71.4) | 94 (79.3) | 92 (79.3) | 269 (76.6) |
| Age (years) |  |  |  |  |  |
| n | 121 | 119 | 116 | 116 | 351 |
| Mean (SD) | 52.2 (11.9) | 53.3 (13.5) | 52.6 (12.0) | 54.2 (13.9) | 53.4 (13.2) |
| Duration of RA (years) |  |  |  |  |  |
| n | 121 | 118 | 116 | 116 | 350 |
| Mean (SD) | 3.7 (2.4) | 4.3 (2.2) | 4.2 (2.4) | 3.9 (2.5) | 4.1 (2.4) |
| Rheumatoid Factor Positive n (%) | 84 (69.4) | 84 (70.6) | 80 (69.0) | 80 (69.0) | 244 (69.5) |
| Erosions Present n (%) | 90 (74.4) | 91 (76.5) | 86 (74.1) | 80 (69.0) | 257 (73.2) |
| Previous DMARD Use n (%) | 98 (81.0) | 94 (79.0) | 87 (75.0) | 77 (66.4) | 258 (73.5) |
| Corticosteriod Use –n(%) | 48 (39.7) | 58 (48.7) | 47 (40.5) | 48 (41.4) | 153 (43.6) |
| NSAID Use n (%) | 106 (87.6) | 95 (79.8) | 97 (83.6) | 96 (82.8) | 288 (82.1) |

N  Number of patients randomized

FIG. 3

Baseline Demographics and Disease
History of Anemic Patients* by Treatment Group

|  | Placebo (N = 13) | 30 mg (N = 17) | 75 mg (N = 18) | IL-1ra 150 mg (N = 15) | All (N = 50) |
|---|---|---|---|---|---|
| Sex – n (%) | | | | | |
| Male | 1 (7.7) | 1 (5.9) | 1 (5.6) | 0 (0.0) | 2 (4.0) |
| Female | 12 (92.3) | 16 (94.1) | 17 (94.4) | 15 (100) | 48 (96.0) |
| Age (years) | | | | | |
| n | 13 | 17 | 18 | 15 | 50 |
| Mean (SD) | 47.7 (13.0) | 52.1 (13.1) | 47.8 (13.5) | 51.2 (13.2) | 50.3 (13.1) |
| Duration of RA (years) | | | | | |
| n | 13 | 16 | 18 | 15 | 49 |
| Mean (SD) | 2.2 (1.6) | 4.2 (2.0) | 4.2 (2.2) | 4.2 (2.3) | 4.2 (2.1) |
| Rheumatoid Factor Positive n (%) | 10 (76.9) | 15 (88.2) | 10 (55.5) | 14 (93.3) | 39 (78.0) |
| Erosions Present n (%) | 11 (84.6) | 15 (88.2) | 16 (88.9) | 14 (93.3) | 45 (90.0) |
| Previous DMARD Use n (%) | 11 (84.6) | 15 (88.2) | 14 (77.8) | 11 (73.3) | 40 (80.0) |
| Corticosteroid Use –n(%) | 5 (38.5) | 10 (58.8) | 8 (44.4) | 6 (40.0) | 24 (48.0) |
| NSAID Use n (%) | 11 (84.6) | 12 (70.6) | 18 (100) | 13 (86.7) | 43 (86.0) |

N Number of patients randomized

FIG. 4

Anakinra Therapy Improves Anemia in RA
Number(%) of Anemic* Patients With
Hematocrit Improvement at Week 24

| Hct increase | Placebo (n=13) | Anakinra 30 mg (n=17) | Anakinra 75 mg (n=18) | Anakinra 150 mg (n=15) | Anakinra Total (n=50) |
|---|---|---|---|---|---|
| ≥ 3 vol-% | 2 (15.4%) | 10 (58.8%) | 6 (33.3%) | 5 (33.3%) | 21 (42.0%) |
| ≥ 4 vol-% | 1 (7.7%) | 5 (29.4%) | 4 (22.2%) | 3 (20.0%) | 12 (24.0%) |
| ≥ 5 vol-% | 1 (7.7%) | 3 (17.6%) | 4 (22.2%) | 2 (13.3%) | 9 (18.0%) |
| ≥ 6 vol-% | 1 (7.7%) | 2 (11.8%) | 4 (22.2%) | 1 (6.7%) | 7 (14.0%) |

*Patients with hematocrit ≤ 34% at baseline

FIG. 5

Anakinra May Improve Anemia in RA Independently of Articular Disease

Number (%) of Anemic* Patients Who Are ACR20 Responders at Week 24

| Hct increase | Placebo (n=13) | Anakinra 30 mg (n=17) | Anakinra 75 mg (n=18) | Anakinra 150 mg (n=15) | Anakinra Total (n=50) |
|---|---|---|---|---|---|
| ≥ 3 vol-% | 1 (7.7%) | 5 (29.4%) | 3 (16.6%) | 2 (13.3%) | 10 (20%) |
| ≥ 4 vol-% | 1 (7.7%) | 2 (11.8%) | 2 (11.1%) | 2 (13.3%) | 6 (12%) |
| ≥ 5 vol-% | 1 (7.7%) | 2 (11.8%) | 2 (11.1%) | 1 (6.7%) | 5 (10%) |
| ≥ 6 vol-% | 1 (7.7%) | 1 (5.9%) | 2 (11.1%) | 1 (6.7%) | 4 (8%) |

*Patients with hematocrit ≤ 34% at baseline

FIG. 6

Anakinra May Improve Anemia in RA Independently of Articular Disease

% if Anemic* ACR20 Responders with Hct Improvement at Week 24*

| Hct increase | Placebo | Anakinra 30 mg | Anakinra 75 mg | Anakinra 150 mg | Anakinra Total |
|---|---|---|---|---|---|
| ≥ 3 vol-% | 1/2 (50%) | 5/10 (50%) | 3/6 (50%) | 2/5 (40%) | 10/21 (48%) |
| ≥ 4 vol-% | 1/1 (100%) | 2/5 (40%) | 2/4 (50%) | 2/3 (67%) | 6/12 (50%) |
| ≥ 5 vol-% | 1/1 (100%) | 2/3 (67%) | 2/4 (50%) | 1/2 (50%) | 5/9 (56%) |
| ≥ 6 vol-% | 1/1 (100%) | 1/2 (50%) | 2/4 (50%) | 1/1 (100%) | 4/7 (57%) |

*Patients with hematocrit ≤ 34% at baseline

METHOD OF TREATING ANEMIA BY ADMINISTERING IL-1RA

This application claims the benefit of U.S. Provisional application No. 60/244,792, filed Oct. 31, 2000, which is hereby incorporated by reference.

FIELD OF THE INVENTION

The invention relates to treating blood disorders using an interleukin-1 (IL-1) inhibitor. The invention also relates to methods of treating blood disorders in a mammal using an IL-1 inhibitor, a tumor necrosis factor (TNF) inhibitor, and an erythropoietin (EPO) receptor agonist.

BACKGROUND OF THE INVENTION

Disorders of the blood present many important health concerns. For example, a decreased hematocrit, e.g. low number of red blood cells, decreased volume of red blood cells, or reduced hemoglobin concentration, is indicative of pathological conditions such as, but not limited to, anemia. The symptoms of anemia may include fatigue, dizziness, headache, chest pain, shortness of breath, and depression.

Treatment of blood disorders such as anemia may involve increasing the patient's hematocrit. One method of treating anemia is to give red blood cell transfusions. This procedure, however, can have risks associated with it. Transfusion reactions may occur if blood is not correctly and completely matched between the donor and the patient, and some diseases, especially viral diseases, may be in the blood being transfused. A theoretical concern, not yet proven, is that frequent blood transfusions may damage the immune system, which protects the body from infections.

Regulatory authorities have approved recombinant human erythropoietin for treatment of anemia associated with chronic renal failure (CRF), anemia related to therapy with AZT (zidovudine) in HIV-infected patients, anemia in patients with non-myeloid malignancies receiving chemotherapy, and anemia in patients undergoing surgery to reduce the need of allogenic blood transfusions.

Due to the serious health problems arising from blood disorders, such as those conditions associated with decreased hematocrit, it is of interest to develop other agents capable of treating these disorders. These agents include, but are not limited to, those that increase hematocrit level.

SUMMARY OF THE INVENTION

In certain embodiments, the invention provides methods of raising hematocrit in a mammal comprising administering a therapeutically effective amount of an IL-1 inhibitor. In certain embodiments, the invention provides methods for maintaining hematocrit in a mammal. In certain embodiments, the invention provides methods of treating blood disorders in a mammal comprising administering a therapeutically effective amount of an IL-1 inhibitor.

In certain embodiments, the invention provides methods of treating blood disorders in a mammal comprising administering an IL-1 inhibitor and an EPO receptor agonist. In certain embodiments, the invention provides methods of raising and/or maintaining hematocrit in a mammal comprising administering an IL-1 inhibitor and an EPO receptor agonist. In certain embodiments, the IL-1 inhibitor and EPO receptor agonists can be administered separately, at the same time or at different times. In certain embodiments, the IL-1 inhibitor and EPO receptor agonist can be administered together at the same time.

In certain embodiments, the invention provides methods of treating blood disorders in a mammal comprising administering a TNF inhibitor and an EPO receptor agonist. In certain embodiments, the invention provides methods of raising and/or maintaining hematocrit in a mammal comprising administering a TNF inhibitor and an EPO receptor agonist. In certain embodiments, the TNF inhibitor and EPO receptor agonists can be administered separately, at the same time or at different times. In certain embodiments, the TNF inhibitor and EPO receptor agonist can be administered together at the same time.

In further embodiments, the invention provides methods of treating blood disorders in a mammal comprising administering an IL-1 inhibitor, a TNF inhibitor and an EPO receptor agonist. In certain embodiments, the invention provides methods of raising and/or maintaining hematocrit in a mammal comprising administering an IL-1 inhibitor, a TNF inhibitor and an EPO receptor agonist. In certain embodiments, the IL-1 inhibitor, TNF inhibitor and EPO receptor agonist can be administered separately, at the same time or at different times. In certain embodiments, the IL-1 inhibitor, TNF inhibitor, and EPO receptor agonist can be administered together at the same time. In further embodiments, the TNF inhibitor and IL-1 inhibitor can be replaced with a single molecule (e.g., a P38 inhibitor) that inhibits both TNF and IL-1:

Also provided are pharmaceutical compositions comprising an IL-1 inhibitor; an IL-1 inhibitor and an EPO receptor agonist; an IL-1 inhibitor, a TNF inhibitor, and an EPO receptor agonist; and an inhibitor of IL-1 and TNF (e.g., a P38 inhibitor) and an EPO receptor agonist.

DESCRIPTION OF THE FIGURES

FIG. 1 shows the baseline demographics and disease history of subjects in the study described in Examples 1, 2, and 3 of this application. The data is grouped by treatment type and level.

FIG. 3 shows the baseline demographics and disease history of subjects in the study described in examples 1, 2, and 3 of this application who had rheumatoid arthritis and anemia. The data is grouped by treatment type and level.

FIG. 4 shows the number and percentage of subjects in the study described in examples 1, 2, and 3 of this application who had rheumatoid arthritis and anemia who demonstrated hematocrit improvement at week 24.

FIG. 5 shows the number and percentage of subjects in the study described in Examples 1, 2, and 3 of this application who had rheumatoid arthritis and anemia and who demonstrated hematocrit level increases who also met the ACR20 response criteria. The data is grouped by levels of hematocrit increase.

FIG. 6 compares the number of subjects in the study described in Examples 1, 2, and 3 of this application with rheumatoid arthritis and anemia who showed both hematocrit improvement and ACR20 response with the total number of subjects with rheumatoid arthritis and anemia who demonstrated hematocrit improvement.

FIG. 10 shows the effect of ARANESP™ and Fc-IL-1ra on red blood cell (RBC) numbers in rats afflicted with anemia of chronic disorders in the study described in Example 4 of this application. Treatment of rats from the experimental group with both 100 mg/kg Fc-IL-1ra and 6 μg/kg ARANESP™ increased red blood cell (RBC) numbers (p<0.03) compared to the same dose of 6 μg/kg ARANESP™ alone.

DEFINITIONS

Figure 2:
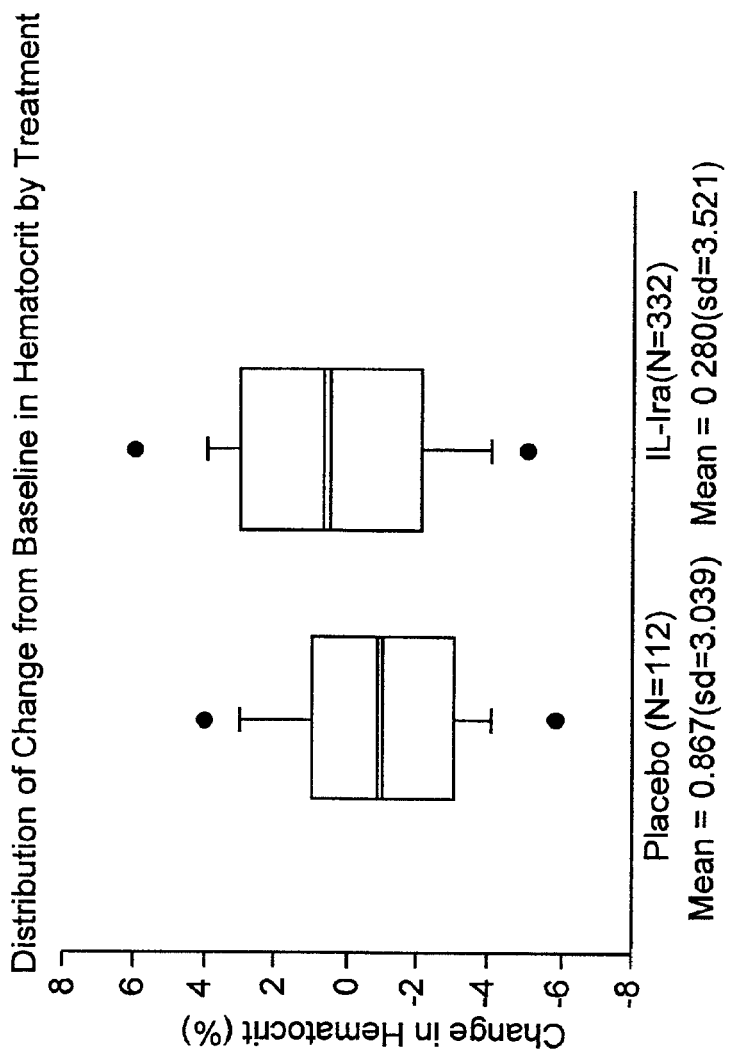
FIG. 2 compares the distribution of change from baseline in hematocrit for treatment with anakinra and treatment with placebo in the study described in Examples 1, 2, and 3 of this application.
Figure 7:
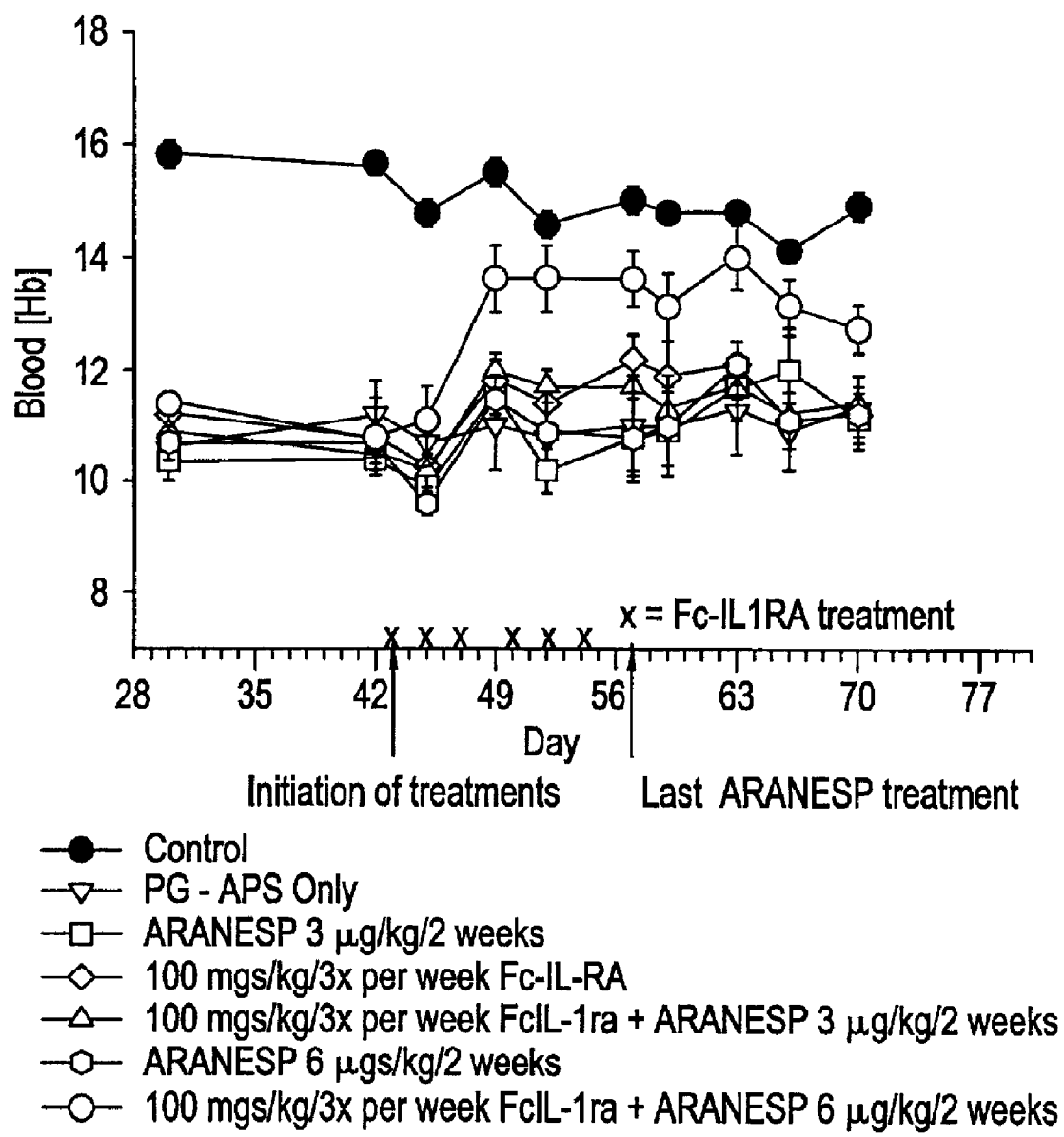
FIG. 7 shows the effect of ARANESP™ (darbepoietin alfa) and Fc-IL-1ra on mean blood hemoglobin concentration in rats afflicted with anemia of chronic disorders in the study described in Example 4 of this application. Combination treatment of Fc-IL-1RA 100 mgs/kg 3×/wk with ARANESP 6 μg/kg/2wks was significantly better at raising blood Hb levels than either single treatment alone (p<0.02)
Figure 8:
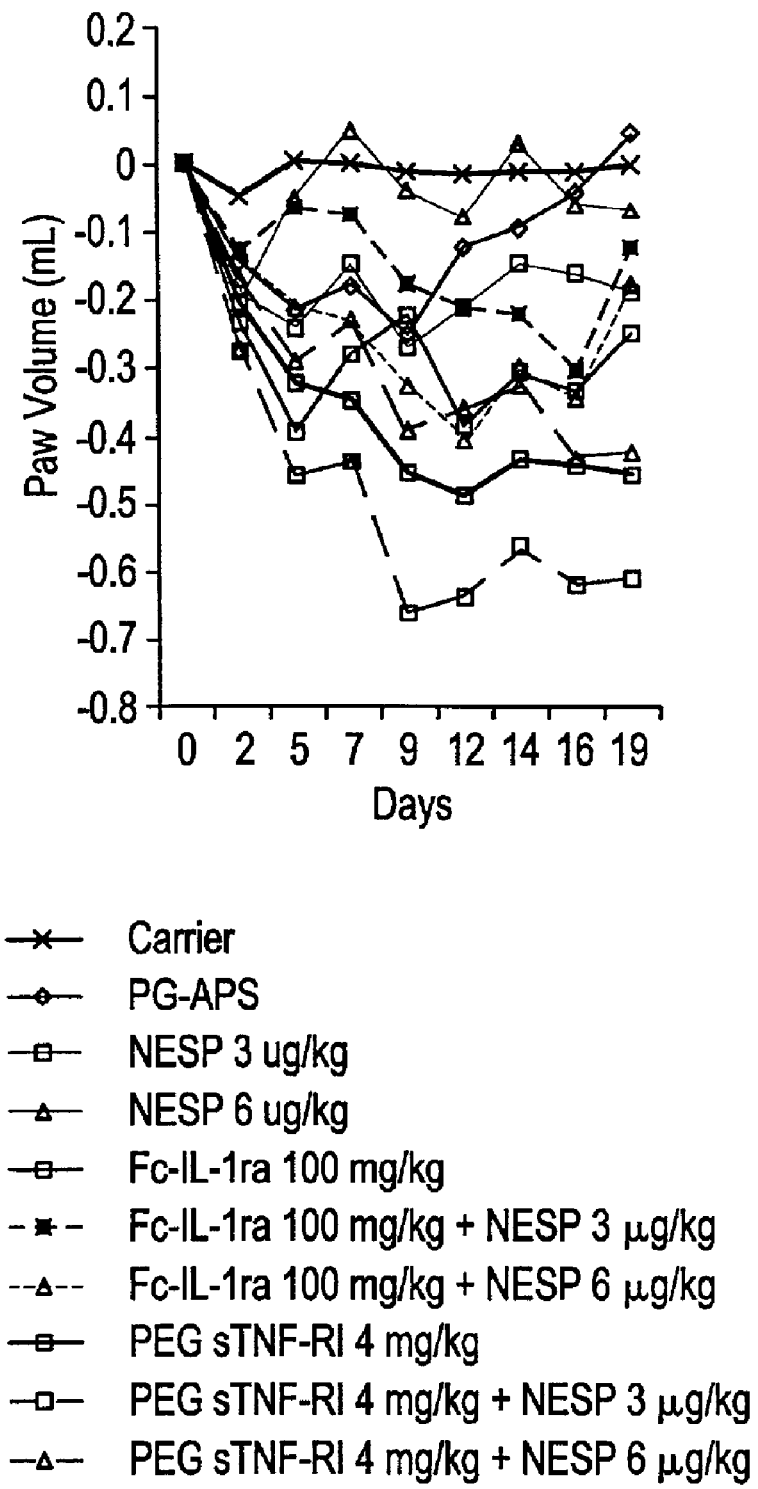
FIG. 8 shows the effect of ARANESP™ alone and with Fc-IL-1ra or a TNF inhibitor (PEG sTNF R1) on paw edema in rats afflicted with anemia of chronic disorders in the study described in Example 4 of this application.

The following definitions apply to the terms as used throughout this specification, unless otherwise limited in specific instances.

"Addition variant" refers to a variant that has at least one more amino acid residue than the parent molecule.

"Adjuvant" is a substance added to a pharmaceutical composition that affects the action of the active ingredient of the composition in a predictable way.

"Administering" refers to any process of introducing a composition into or onto the body of a mammal and includes, but is not limited to, particular methods described in this specification.

"Anemia of chronic diseases" (ACD) refers to any mild to moderately severe anemia that is associated with chronic diseases such as, but not limited to, trauma, infectious and inflammation (e.g., rheumatoid arthritis (RA) or inflammatory bowel disease (IBD)), and neoplastic diseases that persist for greater than 2 months.

"ARANESP™" refers to the super-sialated erythropoietic protein described in published PCT Application No. WO 00/24893 "Methods and Compositions for the Prevention and Treatment of Anemia" (incorporated by reference herein for any purpose) and any derivatives or variants of this protein.

"Chimeric polypeptide" refers to a polypeptide created by the fusion between two or more different polypeptides.

"Deletion variant" refers to a variant that has at least one less amino acid residue than the parent molecule.

"Derivative" refers to a chemically modified protein in which a nonproteinaceous moiety is linked to the protein.

"Diluent" is a substance used to lessen the concentration of the other components of a composition.

"Emulsifier" is an agent such as, but not limited to, a soap, detergent, steroid or a protein used to stabilize an emulsion of a hydrophobic phase and an aqueous phase.

"Erythropoietin (EPO) receptor agonist" refers to molecules capable of causing activation of the EPO receptor, which may result from any number of mechanisms. EPO receptor agonists include those described or referred to in this specification, such as, but not limited to darbepoietin alfa (ARANESP™), epoietin alfa (EPO, EPOGEN®), and anti-EPO receptor agonist antibodies.

"Fc" refers to all or part of the constant domain of the heavy or light chain of human immunoglobulin and any variants or derivatives of this domain.

"Fc-IL-1ra" refers to a molecule comprising the sequences of both IL-1ra and the constant domain of the heavy or light chain of human immunoglobulin and any variants or derivatives of this domain. Exemplary Fc-IL-1ra is described in PCT Application WO 97/28828, published Jun. 14, 1997 (incorporated by reference) and any derivatives or variants of this polypeptide.

"Interleukin-1 (IL-1) inhibitor" refers to molecules capable of specifically inhibiting activation of cellular receptors by IL-1, which may result from any one or more number of mechanisms. Such mechanisms include, but are not limited to, downregulating IL-1 production, binding free IL-1, interfering with IL-1 binding to its receptor, interfering with formation of the IL-1 receptor complex (i.e., association of IL-1 receptor with IL-1 receptor accessory protein), or interfering with modulation of IL-1 signaling after binding to its receptor. Interleukin-1 inhibitors include, but are not limited to, those described or referred to in this specification such as anti-IL-1 receptor antibodies, IL-1 receptor antagonist, and Fc-IL-1ra.

"Parent molecule" refers to an unmodified molecule or a variant molecule lacking the particular variation under discussion. For example, when discussing substitution variants of a parent molecules, the parent molecule may be a deletion variant.

"Preservative" is a substance added to a composition to inhibit chemical change to the composition or contamination of the composition.

"Solubilizer" is a substance added to a composition to increase dissolution of the components of the composition.

"sTNF-RI" refers to a soluble form of the type I (p55) receptor for tumor necrosis factor (TNF) and any fusion proteins, derivatives or variants thereof. Exemplary sTNF-RI is described in WO 98/01555.

"Substitution variant" refers to a variant wherein at least one amino acid residue in a parent molecule is removed and a different residue inserted in its place.

"Therapeutically effective amount" is that amount that results in a measurable improvement of at least one clinical parameter in a mammal afflicted with the particular disorder.

"Variant" refers to a potypeptide with at least 75%, or at least 80%, or at least 90%, or at least 95% or at least 99% amino acid sequence homology to the reference polypeptide and that maintains some level, including a reduced level, of relevant activity of the reference polypeptide. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff (1972), Atlas of Protein Sequence and Structure, 5:124, National Biochemical Research Foundation, Washington, D.C., the disclosure of which is hereby incorporated by reference for any purpose. Variants can be based on a reference polypeptide in which one or more amino acids have been deleted from ("deletion variants"), inserted into ("addition variants"), or substituted within ("substitution variants") the reference molecule.

Within this application, mention of the singular includes the plural unless explicitly indicated otherwise.

DETAILED DESCRIPTION OF THE INVENTION

All documents cited in this application are incorporated by reference herein for any purpose.

In certain embodiments, the invention provides for a method of raising hematocrit in a mammal comprising administering a therapeutically effective amount of an IL-1 inhibitor. In certain embodiments, the invention includes maintaining a raised hematocrit. In certain embodiments, pharmaceutical compositions comprising an IL-1 inhibitor are provided.

The invention, in certain embodiments, provides for treating blood disorders such as, but not limited to, anemias in a mammal comprising administering an IL-1 inhibitor, an IL-1 inhibitor and an EPO receptor agonist, a TNF inhibitor and an EPO receptor agonist, or an IL-1 inhibitor as well as a TNF inhibitor and an EPO receptor agonist. In certain embodiments, the invention provides for raising hematocrit by administering an IL-1 inhibitor and an EPO receptor agonist, a TNF inhibitor and an EPO receptor agonist, or an IL-1 inhibitor as well as a TNF inhibitor and an EPO receptor agonist. In certain embodiments, the invention includes maintaining a raised hematocrit by administering an IL-1 inhibitor and an EPO receptor agonist, a TNF inhibitor and an EPO receptor agonist, or an IL-1 inhibitor as well as a TNF inhibitor and an EPO receptor agonist. In certain embodiments, pharmaceutical compositions comprising an IL-1 inhibitor and an EPO receptor agonist, a TNF inhibitor and an EPO receptor agonist, or an IL-1 inhibitor as well as a TNF inhibitor and an EPO receptor agonist are provided. In further embodiments, methods of treatment of blood disorders using such compositions are provided.

According to certain embodiments, the invention may be employed in treatment of blood disorders, such as, but not limited to, the following:

anemia associated with a decline or loss of kidney function (chronic renal failure);

anemia associated with myelosuppressive therapy, such as chemotherapeutic or anti-viral drugs (such as AZT);

anemia associated with the progression of non-myeloid cancers, anemia associated with viral infections (such as HIV);

anemia associated with relative erythropoietin deficiency;

anemia associated with congestive heart failure; and anemia of chronic disease such as autoimmune disease (e.g., rheumatoid arthritis).

According to certain embodiments, the invention may be employed with conditions that may lead to anemia in an otherwise healthy individual, such as an anticipated loss of blood during surgery. In certain embodiments, treatment includes once daily dosing for anemia associated with rheumatoid arthritis (RA). Blood disorders also include, but are not limited to, disorders of hematopoiesis, hemachromatosis, and deficiencies in iron metabolism. Hematopoiesis refers to the formation of blood or blood cells.

Anemia can occur as an extra-articular complication of rheumatoid arthritis (RA) and usually correlates with markers of disease activity (Peeters HRM et al., *Ann. Rheum. Dis.,* 55:162–68 1996). The inventors found that treatment with an IL-1 inhibitor of patients with RA increased the hematocrit of these patients (FIG. 2). In particular, the hematocrit in those RA patients who were also anemic was increased relative to the placebo (FIG. 4). Furthermore, the inventors found that the hematocrit improved even in those patients whose RA response (known as ACR20) did not meet accepted criteria (FIGS. 5 and 6).

As noted above, one form of anemia is anemia of chronic disease (ACD). ACD is a broad term for mild to moderately severe anemia that is often associated with such conditions as, but not limited to:

trauma;

infectious inflammation;

noninfectious inflammation, such as may be associated with rheumatoid arthritis (RA), inflammatory bowel disease (IBD), lupus (including systemic lupus erythematosus or SLE) multiple sclerosis (MS), congestive heart failure (CHF), cardiovascular inflammation, and neoplastic diseases that persist for greater than two months.

For a review of certain ACD, see Means (1999), *International J. of Hematol.* 70(1):7–12. ACD is known to have a multi-factorial pathogenesis mediated in varying degree by innate and cognate immune response and pro-inflammatory cytokines such as INF-γ, TNF-α, and IL-1 (Means (1999), *International J. of Hematol.* 70(1):7–12; Voulgari, et al., (1999), *Clin. Immunol.* 92:153–160).

Immunization of Lewis rats with peptidoglycan-polysaccharide polymers induces relapsing arthritis and a biphasic ACD that closely replicates human ACD. The inventors found that administration of Fc-IL-1ra with ARANESP™ to these rats increased mean Hb level, reticulocyte number, red blood cell number, corpuscular volume, corpuscular HB level, and total serum iron concentration to a greater extent than either Fc-IL-1ra or ARANESP™ administered alone (see FIGS. 7 to 15).

Figure 16A:
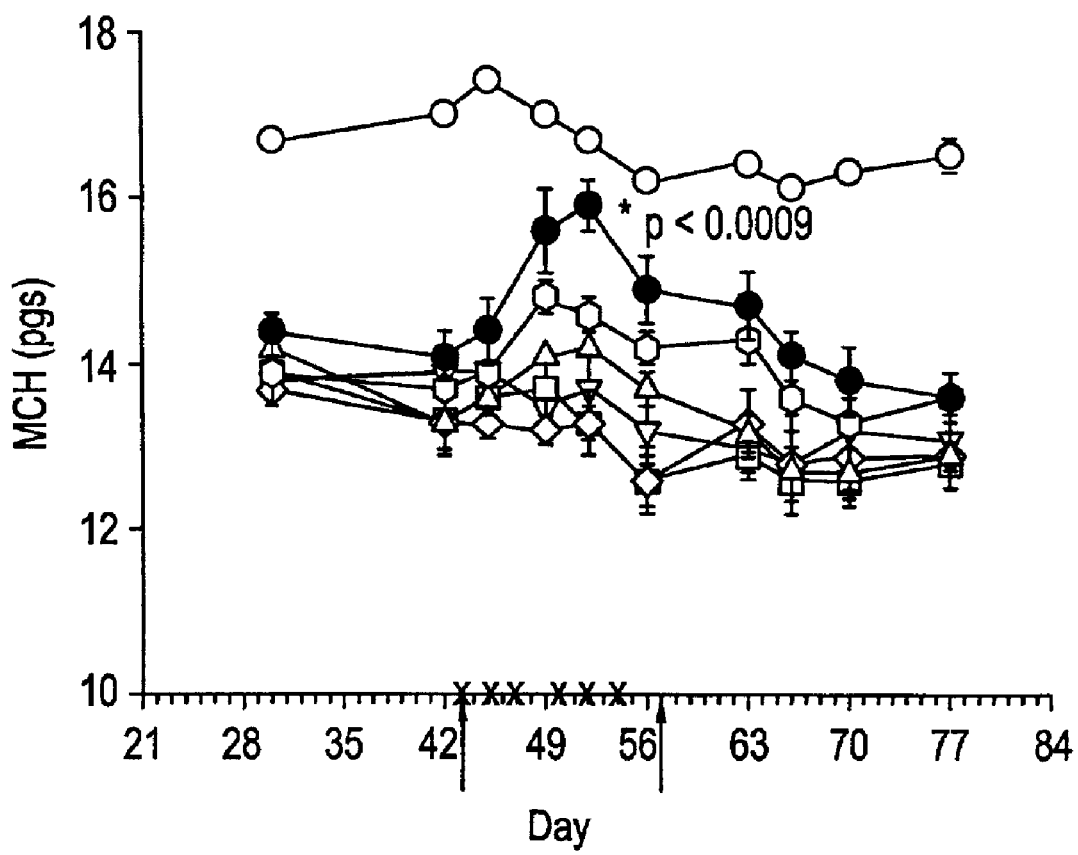
FIG. 16 shows the effect of ARANESP™ and PEG sTNF R1 on MCH and MCV in rats afflicted with anemia of chronic disorders in the study described in Example 4 of this application. Combination treatment of PEG sTNF R1 4 mgs/kg 3×/wk with ARANESP 6 μg/kg/2wks was significantly better at raising MCH (p<0.0009) and MCV (p<0.01) than either single treatment alone.
Figure 16B:
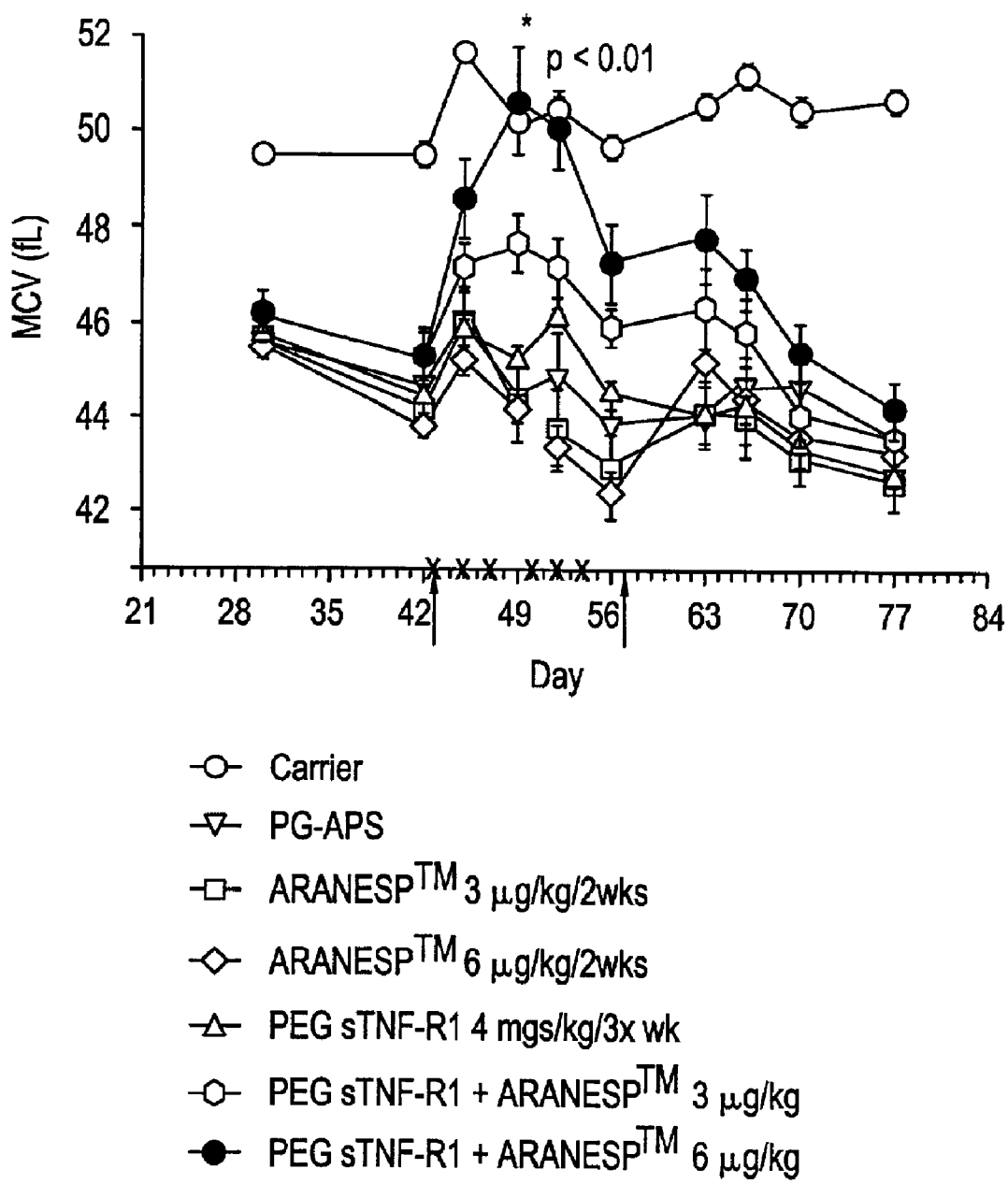
Figure 17A:
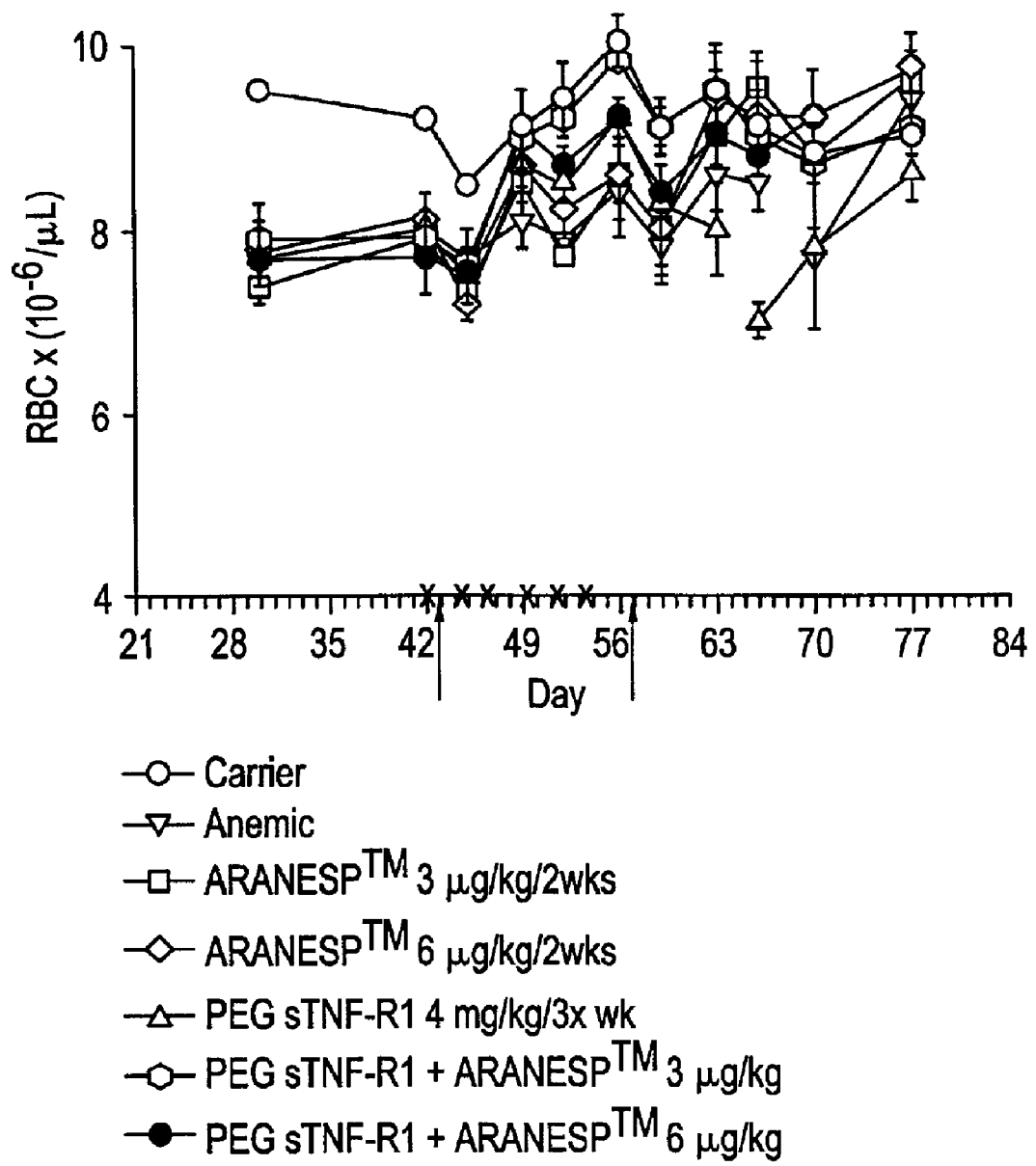
FIG. 17 shows the effect of ARANESP™ and PEG sTNF R1 on mean reticulocyte numbers and RBC numbers in rats afflicted with anemia of chronic disorders in the study described in Example 4 of this application. Combination treatment of PEG sTNF R1 4 mgs/kg 3×/wk with ARANESP 6 μg/kg/2wks was significantly better at raising reticulocyte levels (p<0.002) than either single treatment alone (p<0.00X).
Figure 17B:
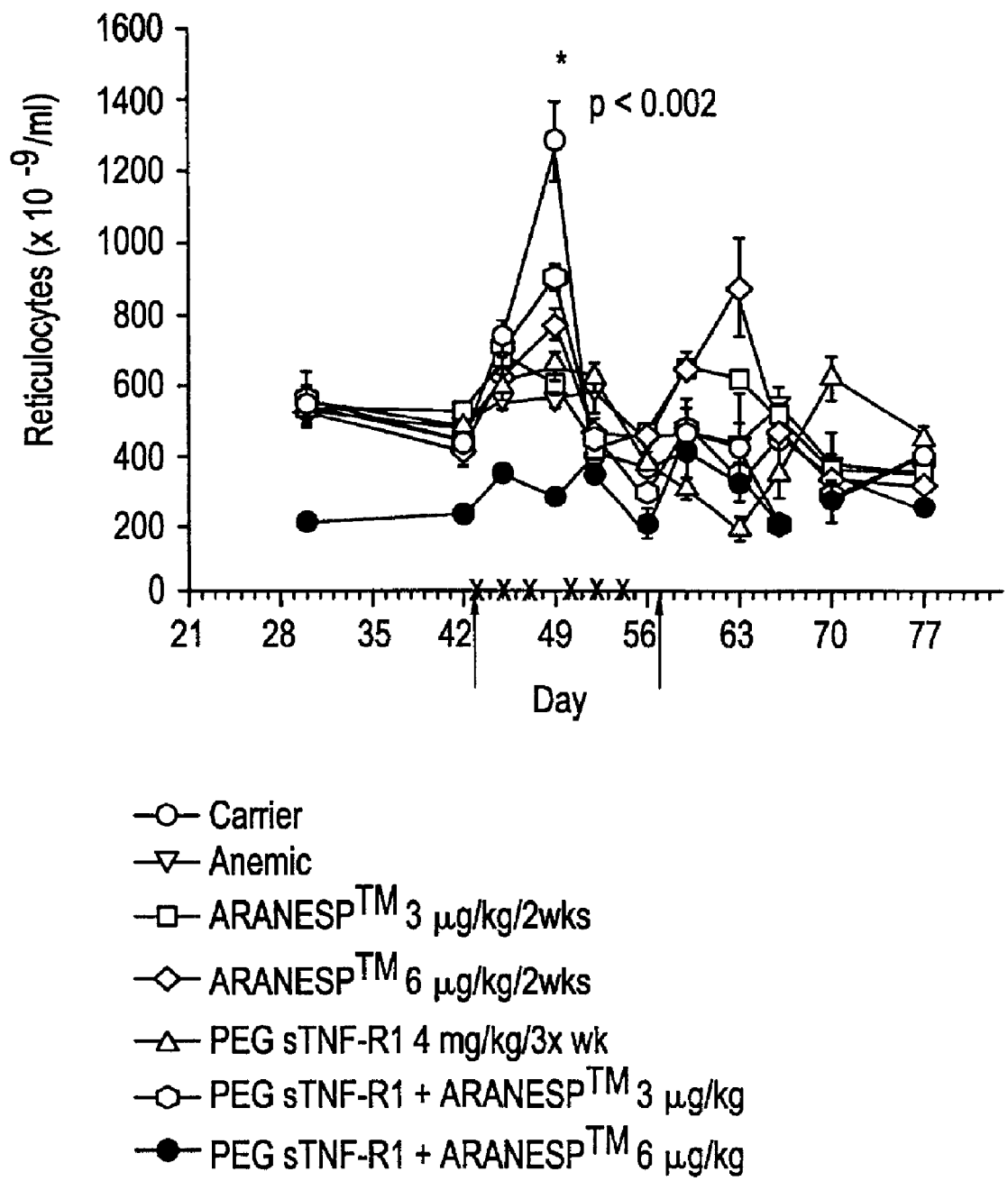
Figure 18A:
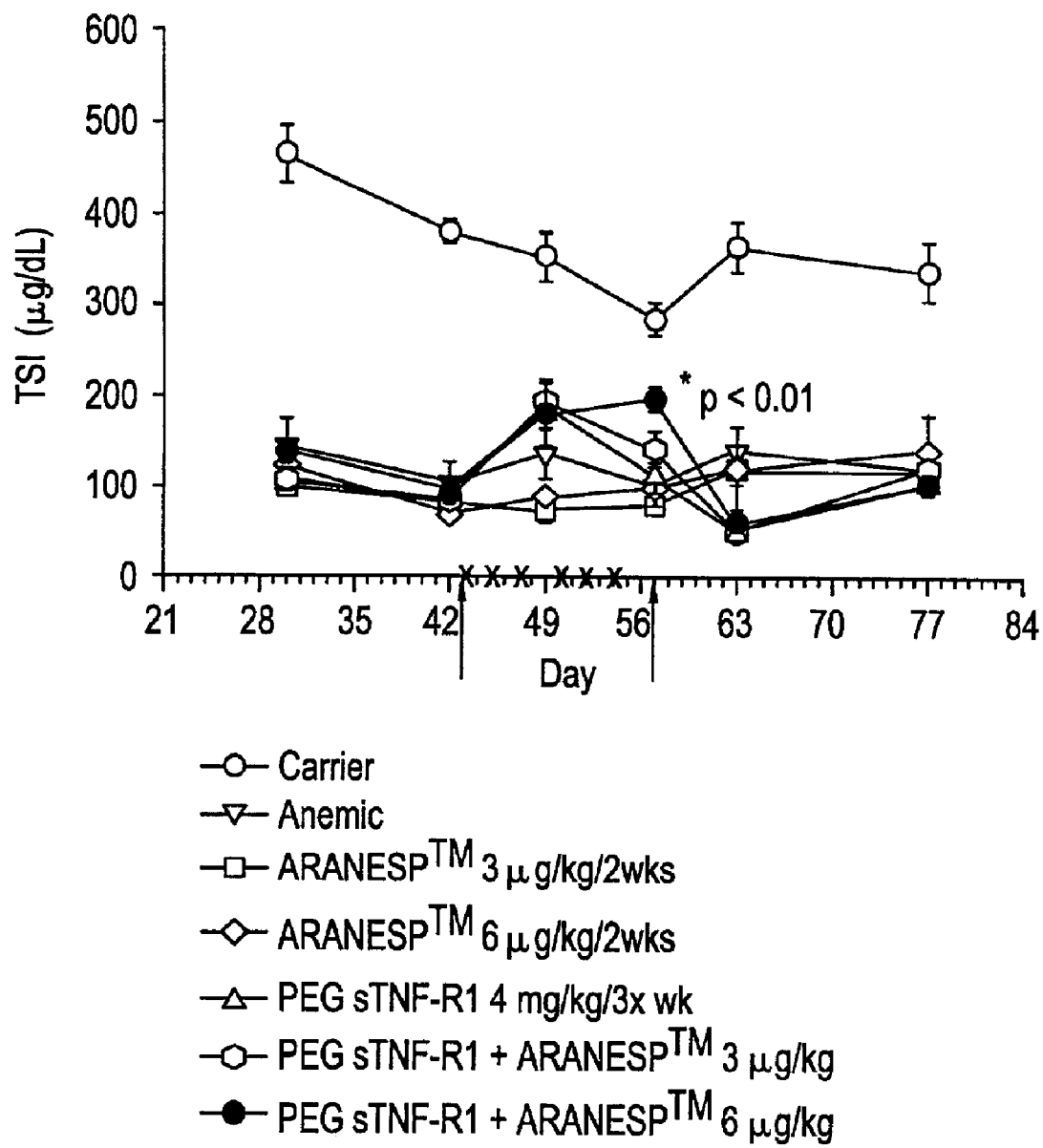
FIG. 18 shows the effect of ARANESP™ and PEG sTNF R1 on TSI and the change in TSI in rats afflicted with anemia of chronic disorders in the study described in Example 4 of this application. Combination treatment of PEG sTNF R1 4 mgs/kg 3×/wk with ARANESP 6 μg/kg/2wks was significantly better at raising serum iron levels than either single treatment alone (p<0.02).
Figure 18B:
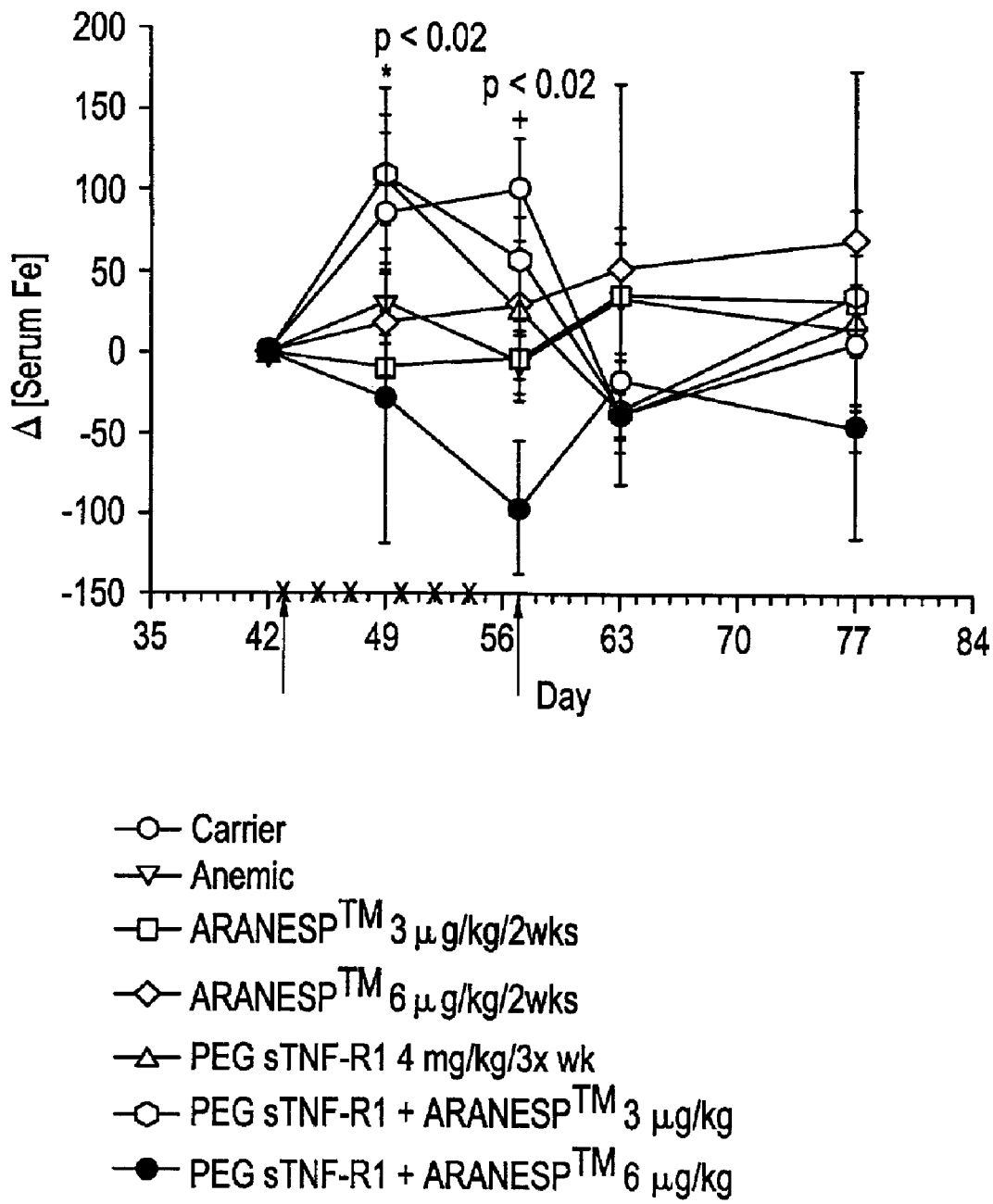
Figure 19:
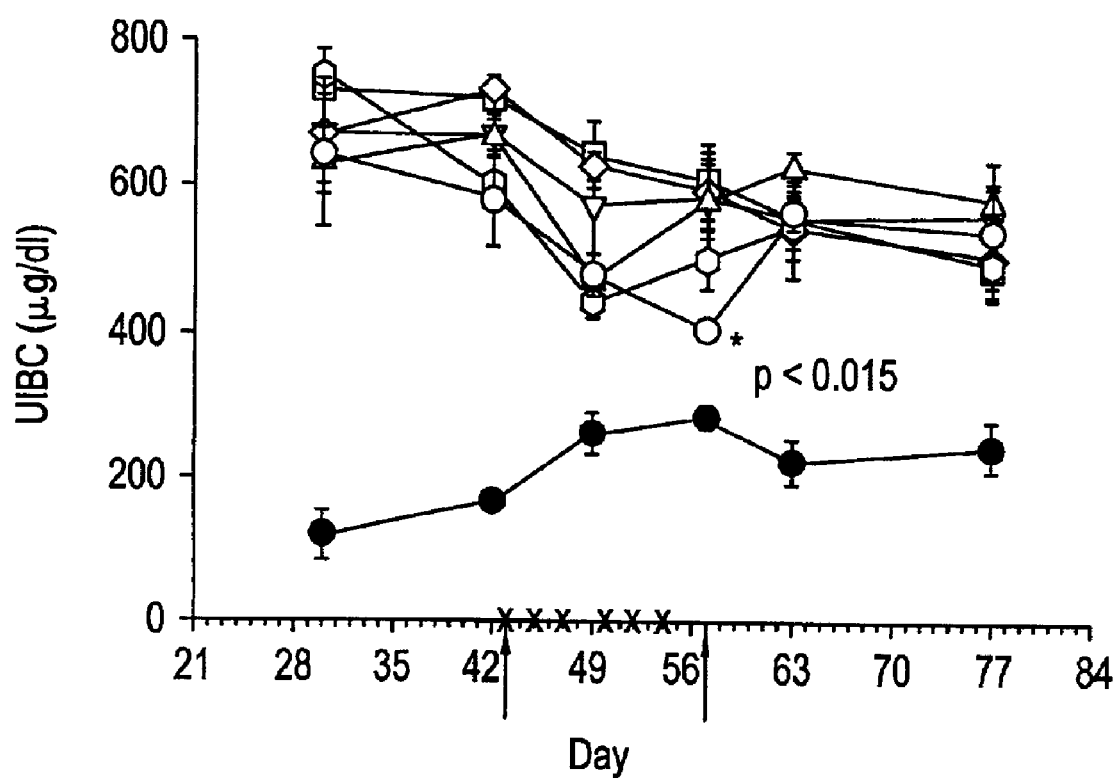
FIG. 19 shows the effect of ARANESP™ and PEG sTNF R1 on the unbound iron binding capacity (UIBC), e.g., serum transferrin levels, in rats afflicted with anemia of chronic disorders in the study described in Example 4 of this application. Combination treatment of PEG sTNF R1 4 mgs/kg 3×/wk with ARANESP 6 μg/kg/2wks generated significantly lower UIBC than either single treatment alone (p<0.015).
Figure 20:
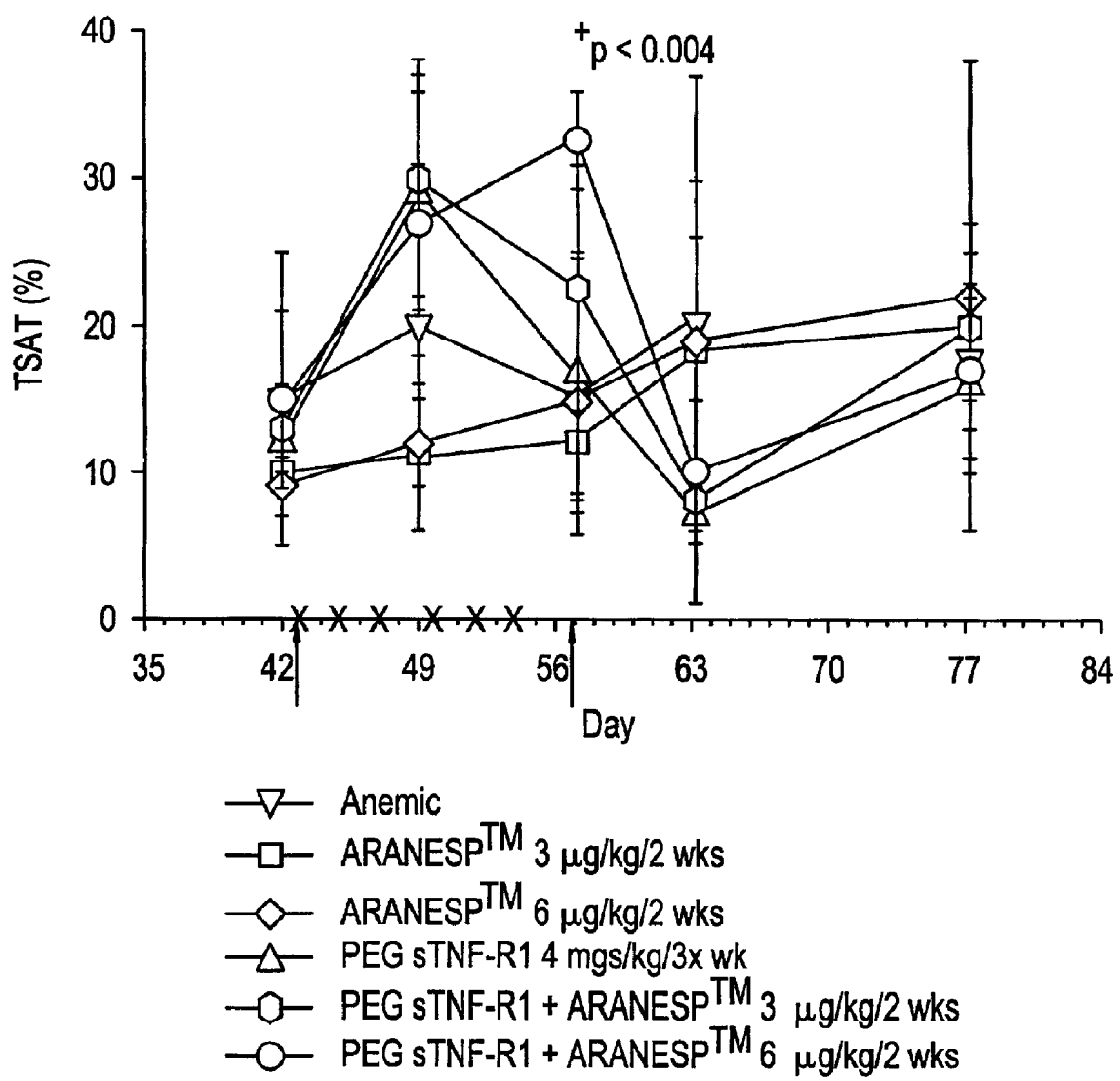
FIG. 20 shows the effect of ARANESP™ and PEG sTNF R1 on transferrin saturation (TSAT) levels (shown as % saturated) in rats afflicted with anemia of chronic disorders in the study described in Example 4 of this application. Combination treatment of PEG sTNF R1 4 mgs/kg 3×/wk with ARANESP 6 μg/kg/2wks was significantly better at raising transferrin saturation than either single treatment alone (p<0.004).

The inventors also administered sTNF-RI alone and in combination with ARANESP™ in the same Lewis rat model of human ACD. The inventors found that rats treated with PEG sTNF-RI only trended toward elevated mean Hb levels (FIG. 16) but had significant reduction in mean paw edema (FIG. 17) compared to untreated rats. Mean Hb levels in rats receiving ARANESP™ treatment alone were elevated over untreated anemic levels. The combined therapies significantly enhanced Hb levels compared to same dose of PEG-sTNF-RI and more than doubled the elevation of Hb compared to the same doses of ARANESP™ alone. The combined therapies also induced more reticulocytes (FIG. 18) and red blood cells (FIG. 19) compared to the same doses of ARANESP™ and PEG-sTNF-RI. The combined therapies increased total serum iron concentrations, corpuscular volume and corpuscular Hb to a greater extent than ARANESP™ alone. The combined therapies also increased total serum iron concentrations, corpuscular volume, and corpuscular Hb more than PEG sTNF-RI alone. While not intending to be constrained by theory, the inventors believe that such results show that the apparent synergistic effect between ARANESP™ and PEG-sTNF-RI is mediated through enhanced erythropoietic response and by enhancing the "hemoglobinization" of the increased numbers of RBCs (i.e., beneficially affecting RBC phagocytosis, iron sequestration and/or iron mobilizaton). In addition, although the data was generated with PEG-sTNF-RI and ARANESP™, other TNF-antagonists (see below) in combination with ARANESP™ or other agonists of epoR (also below) should generate similar results.

The combination therapies of this invention may also be useful in treatment of conditions associated with iron storage disorders. Stored iron is involved in the generation of superoxides and other reactive species which mediate tissue damage in numerous diseases or disorders. For such conditions and disorders, the IL-1 inhibitor or TNF inhibitor may aid release of iron and the EPO receptor agonist may aid consumption of the excess iron by erythropoiesis. For this or other reasons, the claimed combination therapies may be useful in treatment of chronic heart disease, myocardial infarction, stroke, cognitive deficiencies or disorders, hemachromatosis, inflammatory bowel disease, and the like.

EPO Receptor Agonists

Erythropoietin (EPO) receptor agonists are molecules capable of causing activation of the EPO receptor, which may result from any one or more number of mechanisms. EPO receptor agonists include those described or referred to in this specification, such as, but not limited to, ARANESP™, EPO and anti-EPO receptor agonist antibodies.

Interleukin-1 Inhibitors

Interleukin-1 is a protein produced by numerous cell-types, including monocytes and some macrophages. This protein has important physiological effects on a number of different target cells. Interleukin-1 inhibitors include, but not are limited to, molecules capable of specifically preventing activation of cellular receptors to IL-1, which may result from any one or more number of mechanisms. Such mechanisms include, but are not limited to, downregulating IL-1 production, binding free IL-1, interfering with IL-1 binding to its receptor, interfering with formation of the IL-1 receptor complex (i.e., association of IL-1 receptor with IL-1 receptor accessory protein), or interfering with modulation of IL-1 signaling after binding to its receptor. Classes of interleukin-1 inhibitors include, but are not limited to:

interleukin-1 receptor antagonists such as IL-1ra, discussed below;

anti-IL-1 receptor monoclonal antibodies (e.g., EP 623674, the disclosure of which is hereby incorporated by reference for any purpose);

IL-1 binding proteins such as soluble IL-1 receptors (e.g., U.S. Pat. No. 5,492,888, U.S. Pat. No. 5,488,032, and U.S. Pat. No. 5,464,937, U.S. Pat. No. 5,319,071, and U.S. Pat. No. 5,180,812, the disclosures of which are hereby incorporated by reference for any purpose);

anti-IL-1 monoclonal antibodies (e.g., WO 9501997, WO 9402627, WO 9006371, U.S. Pat. No. 4,935,343, EP 364778, EP 267611 and EP 220063, the disclosures of which are hereby incorporated by reference for any purpose);

IL-1 receptor accessory proteins and antibodies thereto (e.g., WO 96/23067 and WO 99/37773, the disclosures of which are hereby incorporated by reference for any purpose);

inhibitors of interleukin-1 beta converting enzyme (ICE) or caspase I (e.g., WO 99/46248, WO 99/47545, and WO 99/47154, the disclosures of which are hereby incorporated by reference for any purpose), which can be used to inhibit IL-1 beta production and secretion;

interleukin-1 beta protease inhibitors;
and other compounds and proteins which block in vivo synthesis or extracellular release of IL-1.

Exemplary IL-1 inhibitors are disclosed in the following references:

U.S. Pat. Nos. 5,747,444; 5,359,032; 5,608,035; 5,843,905; 5,359,032; 5,866,576; 5,869,660; 5,869,315; 5,872,095; 5,955,480; 5,965,564;

International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, 99/36415;

European (EP) patent applications 534978 and 894795; and

French patent application FR 2762514.

The disclosures of all of the aforementioned references are hereby incorporated by reference for any purpose.

Certain embodiments of the invention provide variants of IL-1 inhibitors, which do not substantially adversely affect the ability to use them to treat anemia. Such additions, deletions, and substitutions may be at the N-terminal or C-terminal of the polypeptide, or may be internal to it. In general, relatively small deletions or additions are less likely to affect structure and/or function of IL-1 inhibitors. In certain embodiments, deletions, additions, or substitutions can be from 5–10 amino acid residues, from 2–5 amino acid residues, or from 1–2 amino acid residues.

The molecules described in the above references and the variants and derivatives thereof discussed hereinafter are collectively termed "IL-1 inhibitors."

Interleukin-1 Receptor Antagonist

Interleukin-1 receptor antagonist (IL-1ra) is a human protein that acts as a natural inhibitor of interleukin-1 and that is a member of the IL-1 family, which includes, but is not limited to, IL-1α and IL-1β. Certain receptor antagonists (including IL-1ra and variants and derivatives, e.g., thereof), as well as methods of making and using thereof, are described in U.S. Pat. No. 5,075,222; WO 91/08285; WO 91/17184; AU 9173636; WO 92/16221; W0 93/21946; WO 94/06457; WO 94/21275; FR 2706772; WO 94/21235; DE 4219626, WO 94/20517; WO 96/22793; WO 97/28828; and WO 99/36541, the disclosures of which are incorporated herein by reference for any purpose.

Specifically, U.S. Pat. No. 5,075,222 describes several forms of IL-1ra. One of those, IL-1raα, called "IL-1i" in the '222 patent, is characterized as a 22–23 kD molecule on SDS-PAGE with an approximate isoelectric point of 4.8, eluting from a Mono Q FPLC column at around 52 mM NaCl in Tris buffer, pH 7.6. Another, IL-1raβ, is characterized as a 22–23 kD protein, eluting from a Mono Q column at 48 mM NaCl. Both IL-1raα and IL-1raβ are glycosylated. A third, IL-1rax, is characterized as a 20 kD protein, eluting from a Mono Q column at 48 mM NaCl, and is non-glycosylated. The U.S. Pat. No. 5,075,222 also discloses certain methods for isolating genes responsible for coding the inhibitors, cloning genes in suitable vectors and cell types, and expressing genes to produce the inhibitors. The proteins include glycosylated as well as non-glycosylated IL-1 receptor antagonists. In certain embodiments, glycosylated IL-1 receptor antagonists may be expressed in human cells, COS cells, or CHO cells. For purposes of the present invention, IL-1ra and variants and derivatives thereof as discussed hereinafter are collectively termed "IL-1ra protein(s)".

TNF-α Inhibitors

TNF-α inhibitors may act by downregulating or inhibiting TNF production, binding free TNF, interfering with TNF binding to its receptor, or interfering with modulation of TNF signaling after binding to its receptor. The term "TNF-α inhibitor" thus includes solubilized TNF receptors, antibodies to TNF, antibodies to TNF receptor, inhibitors of TNF-α converting enzyme (TACE), and other molecules that affect TNF activity. Well known TNF-α inhibitors within the scope of this invention include, but are not limited to the following:

TNF-α neutralizing antibodies such as infliximab (REMICADE®) and D2E7;

antibody fragments such as CDP 870;

TNF-α receptor antagonist Abs;

soluble TNF-RI molecules such as onercept;

soluble TNF-RII molecules such as etanercept (ENBREL®);

TNF-α production inhibitors; and small molecule inhibitors such as P38 inhibitors.

TNF-α inhibitors of various kinds are disclosed in the art, including the following references:

European patent applications EP 308 378; EP 422 339,; GB 2 218 101, EP 393 438;, WO 90/13575, EP 398 327, EP; 412 486, WO 91/03553, EP; 418 014, 417 563, JP 127,800/ 1991, EP 433 900, U.S. Pat. No. 5,136,021, GB 2 246 569,; EP 464 533;, WO 92/01002, WO 92/13095, WO 92/16221, EP 512 528;, EP 526 905;, WO 93/07863, EP 568 928; EP 607 776 (use of leflunomide for inhibition of TNF-α); , 663 210; 542 795; 818 439; 664 128; 542 795; 741 707; 874 819 ; 882 714; 880 970; 648 783; 731 791; 895 988; 550 376; 882 714; 853 083; 550 376; 943 616; 939 121; 614 984; 853 083

U.S. Pat. Nos. 5,136,021; 5,929,117; 5,948,638; 5,807,862; 5,695,953; 5,834,435; 5,817,822; 5830742; 5,834,435; 5,851,556; 5,853,977; 5,359,037; 5,512,544; 5,695,953; 5,811,261; 5,633,145; 5,863,926; 5,866,616; 5,641,673; 5,869,677; 5,869,511; 5,872,146; 5,854,003; 5,856,161; 5,877,222; 5,877,200; 5,877,151; 5,886,010; 5,869,660; 5,859,207; 5,891,883; 5,877,180; 5,955,480; 5,955,476; 5,955,435; 5,994,351; 5,990,119; 5,952,320; 5,962,481;

International(WO)patent applications 90/13575, 91/03553, 92/01002, 92/13095, 92/16221, 93/07863, WO 93/21946, WO 93/19777, EP 417 563, WO 95/34326, WO 96/28546, 98/27298, 98/30541, 96/38150, 96/38150, 97/18207, 97/15561, 97/12902, 96/25861, 96/12735, 96/11209, 98/39326, 98/39316, 98/38859, 98/39315, 98/42659, 98/39329, 98/43959, 98/45268, 98/47863, 96/33172, 96/20926, 97/37974, 97/37973, 97/47599, 96/35711, 98/51665, 98/43946, 95/04045, 98/56377, 97/12244, 99/00364, 99/00363, 98/57936, 99/01449, 99/01139, 98/56788, 98/56756, 98/53842, 98/52948, 98/52937, 99/02510, 97/43250, 99/06410, 99/06042, 99/09022, 99/08688, 99/07679, 99/09965, 99/07704, 99/06041, 99/37818, 99/37625, 97/11668, 99/50238, 99147672, 99/48491;

Japanese (JP) patent applications 10147531, 10231285, 10259140, and 10130149, 10316570, 11001481, and 127, 800/1991;

German (DE) application 19731521;

British (GB) applications 2 218 101, 2 326 881, 2 246 569 and PCT Application No. PCT/US97/12244.

For purposes of this invention, the molecules disclosed in these references and the sTNFRs and variants and derivatives of the sTNFRs and the molecules disclosed in the references below are collectively termed "TNF-α inhibitors."

For example, EP 393 438 and EP 422 339 teach the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), collectively termed "sTNFRs", as well as modified forms thereof (e.g., fragments, functional derivatives and variants). EP 393 438 and EP 422 339 also disclose methods for isolating the genes responsible for coding the inhibitors, cloning the gene in suitable vectors and cell types, and expressing the gene to produce the inhibitors.

sTNFR-I and sTNFR-II are members of the nerve growth factor/TNF receptor superfamily of receptors which includes the nerve growth factor receptor (NGF), the B cell antigen CD40, 4-1 BB, the rat T-cell antigen MRC OX40, the fas antigen, and the CD27 and CD30 antigens (Smith et al. (1990), *Science,* 248:1019–1023). The most conserved feature amongst this group of cell surface receptors is the cysteine-rich extracellular ligand binding domain, which can be divided into four repeating motifs of about forty amino acids and which contains 4–6 cysteine residues at positions which are well conserved (Smith et al. (1990), *supra*).

EP 393 438 teaches a 40 kDa TNF inhibitor Δ51 and a 40 kDa TNF inhibitor Δ53, which are truncated versions of the full-length recombinant 40 kDa TNF inhibitor protein wherein 51 or 53 amino acid residues, respectively, at the carboxyl terminus of the mature protein are removed.

PCT Application No. PCT/US97/12244 teaches truncated forms of sTNFR-I and sTNFR-II which do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, which do not contain a portion of the first domain (amino acid residues $Asp^{1}$-$Cys^{19}$ of sTNFR-I and amino acid residues $Leu^{1}$-$Cys^{32}$ of sTNFR-II). The truncated sTNFRs of the present invention include the proteins represented by the formula $R_1$-[$Cys^{19}$-$Cys^{103}$]-$R_2$ and $R_4$-[$Cys^{32}$-$Cys^{115}$]-$R_5$. These proteins are truncated forms of sTNFR-I and sTNFR-II, respectively.

By "$R_1$-[$Cys^{19}$-$Cys^{103}$]-$R_2$" is meant one or more proteins wherein [$Cys^{19}$-$Cys^{103}$] represents residues 19 through 103 of sTNFR-I, the amino acid residue numbering scheme of which is provided in FIG. 1 to facilitate the comparison; wherein $R_1$ represents a methionylated or nonmethionylated amine group of $Cys^{19}$ or of amino-terminus amino acid residue(s) selected from any one of $Cys^{18}$ to $Asp^{1}$ and wherein $R_2$ represents a carboxy group of $Cys^{103}$ or of carboxy-terminal amino acid residues selected from any one of $Phe^{104}$ to $Leu^{110}$.

Exemplary truncated sTNFR-I of the present invention include the following molecules (collectively termed 2.6D sTNFR-I): $NH_2$-[$Asp^{1}$-$Cys^{105}$]-COOH (also referred to as sTNFR-I 2.6D/C105); $NH_2$-[$Asp^{1}$-$Leu^{108}$]-COOH (also referred to as sTNFR-I 2.6D/C106); $NH_2$-[$Asp^{1}$-$Asn^{105}$]-COOH (also referred to as sTNFR-I 2.6D/N105); $NH_2$-[$Tyr^{9}$-$Leu^{108}$]-COOH (also referred to as sTNFR-I 2.3D/d8); $NH_2$-[$Cys^{19}$-$Leu^{108}$]-COOH (also referred to as sTNFR-I 2.3D/d18); and $NH_2$-[$Ser^{16}$-$Leu^{108}$]-COOH (also referred to as sTNFR-I 2.3D/d15), either methionylated or nonmethionylated, and variants and derivatives thereof.

By "$R_3$-[$Cys^{32}$-$Cys^{115}$]-$R_4$" is meant one or more proteins wherein [$Cys^{32}$-$Cys^{115}$] represents residues $Cys^{32}$ through $Cys^{115}$ of sTNFR-II, the amino acid residue numbering scheme of which is provided in FIG. 2 to facilitate the comparison; wherein $R_3$ represents a methionylated or non-methionylated amine group of $Cys^{32}$ or of amino-terminus amino acid residue(s) selected from any one of $Cys^{31}$ to $Leu^{1}$ and wherein $R_4$ represents a carboxy group of $Cys^{115}$ or of carboxy-terminal amino acid residue(s) selected from any one of $Ala^{116}$ to $Arg^{122}$.

Variants of Proteins

Variant refers a polypeptide with at least 75%, or at least 80%, or at least 90%, or at least 95% or at least 99% amino acid sequence homology to the reference polypeptide and that maintains some level, including a reduced level, of relevant activity of the reference polypeptide. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff (1972), *Atlas of Protein Sequence and Structure,* 5:124, National Biochemical Research Foundation, Washington, D.C., the disclosure of which is hereby incorporated by reference for any purpose. Also included within the term "substantially homologous" are variant(s) of parent molecules that may be isolated by cross-reactivity with antibodies to the parent molecule amino acid sequences or whose genes may be isolated through hybridization with the DNA of parent molecules or segments thereof under highly stringent or moderately stringent hybridization conditions.

Those skilled in the art will understand that one may make many variants based on IL-1 inhibitors or EPO receptor agonists in which amino acids have been deleted ("deletion variants"), inserted ("addition variants"), and/or substituted ("substitution variants"). Such variants should, however, maintain at some level (including a reduced level) certain relevant activity of the unmodified or "parent" molecule and thus may be used as IL-1 inhibitors or EPO receptor agonists.

Variants may be prepared by a variety of mutagenesis techniques available to one skilled in the art, such as, but not limited to, site-directed mutagenesis, PCR mutagenesis, and cassette mutagenesis (Zoller et al. Meth. Enz. 100, 468–500 (1983); Higuchi, in *PCR Protocols* pp. 177–183 (Academic Press, 1990); Wells et al. Gene 34, 315–323 (1985)). Variants may be rapidly screened to assess their physical properties. It will be appreciated that such variant(s) will demonstrate similar properties to the unmodified molecule, but not necessarily all of the same properties and not necessarily to the same degree as the corresponding parent molecule.

There are typically two principal variables in the construction of amino acid sequence variant(s): the location of the mutation site and the nature of the mutation. In designing variant(s), the location of each mutation site and the nature of each mutation may depend on the biochemical characteristic(s) to be modified. In certain embodiments, each mutation site can be modified individually or in series, e.g., by (1) deleting the target amino acid residue, (2) inserting one or more amino acid residues adjacent to the located site, or (3) substituting first with conservative amino acid choices and, depending upon the results achieved, then with more radical selections.

In certain embodiments, amino acid sequence deletions range from about 1 to 30 amino acid residues, from about 1 to 20 amino acid residues, from about 1 to 10 amino acid residues, or from about 1 to 5 contiguous amino acid residues. Deletions include, but are not limited to, amino-terminal, carboxy-terminal and internal intrasequence. In the case of IL-1ra, in certain embodiments, deletions may be made in regions of low homology in the IL-1 family (which comprises IL-1α, IL-1β and IL-1ra). Deletions in areas of substantial homology with other members of the family typically will be more likely to significantly modify the biological activity.

In certain embodiments, an amino acid sequence addition may include insertions of an amino- and/or carboxyl-terminal fusion ranging in length from one residue to one hundred or more residues, as well as internal intrasequence insertions of single or multiple amino acid residues. In certain embodiments, internal additions may range from about 1 to 20 amino acid residues, from about 1 to 10 amino acid residues, from about 1 to 5 amino acid residues, or from about 1 to 3 amino acid residues.

An amino-terminus addition is contemplated to include, but not be limited to, the addition of a methionine (for example, as an artifact of the direct expression in bacterial recombinant cell culture). A further example of an amino-terminal addition includes, but is not limited to, the fusion of a signal sequence to the amino-terminus of a mature molecule in order to facilitate its secretion from recombinant host cells. Such signal sequences typically will be obtained from and thus be homologous to the intended host cell species. For prokaryotic host cells that do not recognize and process the native signal sequence of the mature molecule, the signal sequence may be substituted by a prokaryotic signal sequence selected in certain embodiments. In certain embodiments, the native signal sequence may be substituted by, for example, the alkaline phosphatase, penicillinase or heat-stable enterotoxin II leader sequences. For expression in yeast cells, in certain embodiments, the signal sequence may be selected from the yeast invertase, alpha factor, or acid phosphatase leader sequences. For mammalian cell expression, in certain embodiments, the native signal sequences are satisfactory, although other mammalian signal sequences may be suitable.

According to certain embodiments, amino- or a carboxy-terminus additions may include chimeric proteins comprising the amino-terminal or carboxy-terminal fusion of IL-1 inhibitor parent molecules or EPO receptor agonist parent molecules with all or part of the constant domain of the heavy or light chain of human immunoglobulin (individually or collectively, ("Fc variant(s)"). In certain embodiments, the immunoglobulin portion of each chimeric protein comprises all of the domains except the first domain of the constant region of the heavy chain of human immunoglobulin such as IgG (e.g., IgG1 or IgG3), IgA, IgM, or IgE. For example, in certain embodiments, an IL-1 inhibitor is a chimeric protein comprising IL-1ra and an $F_c$ domain, particularly that of a human IgG1. See, for example, WO 97/28828, which is hereby incorporated by reference for any purpose. A skilled artisan will appreciate that, in certain embodiments, any amino acid of the immunoglobulin portion can be deleted or substituted with one or more amino acids, or one or more amino acids can be added as long as the parent molecule still maintains some level of its relevant activity and the immunoglobulin portion shows one or more of its characteristic properties.

Another group of variants is the amino acid substitution variants. These are variants wherein at least one amino acid residue in a parent molecule is removed and a different residue inserted in its place. Substitution variants include, but are not limited to, allelic variants which are characterized by naturally-occurring nucleotide sequence changes in the species population that may or may not result in an amino acid change. One skilled in the art can use any information known about the binding or active site of the polypeptide in the selection of possible mutation sites.

In certain embodiments, one method for identifying amino acid residues or regions for mutagenesis of a protein is called "alanine scanning mutagenesis", as described by Cunningham and Wells (1989), *Science,* 244:1081–1085, the disclosure of which is hereby incorporated by reference for any purpose. In this method, an amino acid residue or group of target residues is identified (e.g., charged residues such as Arg, Asp, His, Lys and Glu) and replaced by a neutral or negatively-charged amino acid (most preferably alanine or polyalanine) to affect the interaction of the amino acids with the surrounding aqueous environment in or outside the cell. Those domains/residues demonstrating functional sensitivity to the substitutions are then refined by introducing additional or alternate residues at the sites of substitution. Thus, the site for introducing an amino acid sequence modification is predetermined. To optimize the performance of a mutation at a given site, alanine scanning or random mutagenesis may be conducted and the variant(s) may be screened for the optimal combination of desired activity and degree of activity in certain embodiments.

The sites typically of greatest interest for substitutional mutagenesis include, but are not limited to, sites in which particular amino acid residues within a parent molecule are substantially different from other species or other family members in terms of side-chain bulk, charge and/or hydrophobicity. Other sites of interest include those in which particular residues of a parent molecule are identical among other species or other family members, as such positions are typically important for the biological activity of a protein.

In certain embodiments, a skilled artisan will appreciate that initially sites typically can be modified by substitution in a relatively conservative manner. Conservative amino acid changes may involve substitution of one amino acid with another that is similar in structure and/or function (e.g., amino acids with side chains similar in size, charge and shape). Examples of such conservative substitutions include, but are not limited to, those shown in Table 1 under the heading of "Preferred Substitutions". If such substitutions do not result in a substantial change in biological activity, then more substantial changes (Exemplary Substitutions) may be introduced and/or other additions/deletions may be made and the resulting products screened.

TABLE 1

Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

In making such changes, the hydropathic index of amino acids may be considered in certain embodiments. The importance of the hydropathic amino acid index in conferring interactive biological function on a protein is generally understood in the art (Kyte and Doolittle (1982), *J. Mol. Biol.,* 157:105–131, the disclosure of which is incorporated herein by reference for any purpose). It is known that certain amino acids may be substituted for other amino acids having a similar hydropathic index or score and still retain a similar biological activity.

It is also understood in the art that the substitution of like amino acids can be made effectively on the basis of hydrophilicity, particularly where the functionally equivalent protein or peptide thereby created is intended for use in immunological embodiments. U.S. Pat. No. 4,554,101, the disclosure of which is incorporated herein by reference for any purpose, states that the greatest local average hydrophilicity of a protein, as governed by the hydrophilicity of its adjacent amino acids, correlates with its immunogenicity and antigenicity, i.e., with a biological property of the protein.

In contrast, in certain embodiments, substantial modifications in the functional and/or chemical characteristics of a parent molecule may be accomplished by selecting substitutions that differ significantly in their effect on maintaining (a) the structure of the polypeptide backbone in the area of the substitution, for example, as a sheet or helical conformation, (b) the relative charge or hydrophobicity of the protein at the target site or (c) the bulk of the side chain. Naturally-occurring residues can be divided into groups based on common side chain properties:

1) hydrophobic: norleucine, Met, Ala, Val, Leu, lle;
2) neutral hydrophilic: Cys, Ser, Thr;
3) acidic: Asp, Glu;
4) basic: Asn, Gln, His, Lys, Arg;
5) aromatic: Trp, Tyr, Phe; and
6) residues that influence chain orientation: Gly, Pro.

Non-conservative substitutions may involve the exchange of a member of one of these groups for another.

Polypeptide Derivatives

In certain embodiments, this invention also comprises chemically modified derivatives of the parent molecules of the IL-1 inhibitor, TNF-α inhibitor, and EPO receptor agonist, and the uses thereof, in which the protein is linked to a nonproteinaceous moiety (e.g., a polymer) in order to modify properties. These chemically modified parent molecules are referred to herein as "derivatives". Such derivatives may be prepared by one skilled in the art given the disclosures herein. In certain embodiments, conjugates may be prepared using glycosylated, non-glycosylated or de-glycosylated parent molecule(s) and suitable chemical moieties. In certain embodiments, non-glycosylated parent molecules and water-soluble polymers will be used. In certain embodiments, derivatives encompassed by the invention include post-translational modifications (e.g., N-linked or O-linked carbohydrate chains, processing of N-terminal or C-terminal ends), attachment of chemical moieties to the amino acid backbone, and chemical modifications of N-linked or O-linked carbohydrate chains. In certain embodiments, the polypeptides may also be modified with a detectable label, such as an enzymatic, fluorescent, isotopic or affinity label to allow for detection and isolation of the protein. Such polypeptide derivatives should maintain at some level (including a reduced level) the relevant activity of the parent molecule and so may be used as IL-1 inhibitors or EPO receptor agonists.

In certain embodiments, water-soluble polymers are desirable because the protein to which each is attached typically will not precipitate in an aqueous environment, such as a physiological environment. In certain embodiments, the polymer will be pharmaceutically acceptable for the preparation of a therapeutic product or composition. One skilled in the art will be able to select the desired polymer based on such considerations as, but not limited to, whether the polymer/protein conjugate will be used therapeutically and, if so, the therapeutic profile of the protein (e.g., duration of sustained release; resistance to proteolysis; effects, if any, on dosage; biological activity; ease of handling; degree or lack of antigenicity and other known effects of a water-soluble polymer on a therapeutic proteins).

Suitable, clinically acceptable, water-soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone)polyethylene glycol, polypropylene glycol homopolymers (PPG) and other polyalkylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. As used herein, polyethylene glycol is meant to encompass any of the forms that have been used to derivative other proteins, such as mono-($C_1$–$C_{10}$) alkoxy- or aryloxy-polyethylene glycol. Polyethylene glycol propionaldehyde may have advantages in manufacturing due to its stability in water.

The water-soluble polymers each may be of any molecular weight and may be branched or unbranched. Typically, the higher the molecular weight or the more branches, the higher the polymer:protein ratio. The water-soluble polymers each typically have an average molecular weight of between about 2 kDa to about 100 kDa (the term "about" indicating that in preparations of a water-soluble polymer, some molecules will weigh more, some less, than the stated molecular weight). In certain embodiments, the average molecular weight of each water-soluble polymer is between about 5 kDa and about 40 kDa, between about 10 kDa and about 35 kDa, or between about 15 kDa and about 30 kDa.

In certain embodiments, the protein has polyethylene glycol (PEG) attached because PEG typically has very low toxicity in mammals [Carpenter et al., Toxicol. Appl. Pharmacol., 18, 35–40 (1971)]. A PEG adduct of adenosine deaminase was approved in the United States for use in humans for the treatment of severe combined immunodeficiency syndrome. A second advantage that can be afforded by the conjugation of PEG is that of effectively reducing the immunogenicity and antigenicity of heterologous proteins. For example, in certain embodiments, a PEG adduct of a human protein might be useful for the treatment of disease in other mammalian species without the risk of triggering a severe immune response.

In certain embodiments, polymers such as PEG may be conveniently attached to one or more reactive amino acid residues in a protein such as the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxyl-terminal amino acid, tyrosine side chains, or to activated derivatives of glycosyl chains attached to certain asparagine, serine or threonine residues. Numerous activated forms of PEG suitable for direct reaction with proteins have been described. In certain embodiments, PEG reagents for reaction with protein amino groups include, but are not limited to, active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino, hydrazine or hydrazide groups are useful for reaction with aldehydes generated by periodate oxidation of carbohydrate groups in proteins.

There are a number of attachment methods available to those skilled in the art, including acylation reactions or alkylation reactions with a reactive water-soluble molecule. In certain embodiments, such reactions generate an amino-terminal chemically modified protein. See, for example, EP 0 401 384; Malik et al. (1992), *Exp. Hematol.*, 20:1028–1035; Francis (1992), *Focus on Growth Factors*, 3(2):4–10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459 and the other publications cited herein that relate to pegylation, the disclosures of which are hereby incorporated by reference for any purpose.

In certain embodiments, pegylation also may be specifically carried out using water-soluble polymers having at least one reactive hydroxy group (e.g. polyethylene glycol). In certain embodiments, the water-soluble polymer can be reacted with an activating group, thereby forming an "activated linker" useful in modifying various proteins. The activated linkers can be monofunctional, bifunctional, or multifunctional.

Activating groups which can be used to link the water-soluble polymer to two or more proteins include, but are not limited to, the following: sulfone, maleimide, sulfhydryl, thiol, triflate, tresylate, azidirine, oxirane and 5-pyridyl. Useful reagents having a reactive sulfone group that can be used in the methods include, without limitation, chlorosulfone, vinylsulfone and divinylsulfone. These PEG derivatives typically are stable against hydrolysis for extended periods in aqueous environments at pHs of about 11 or less, and can form linkages with molecules to form conjugates which are also hydrolytically stable. Useful homobifunctional derivatives include, but are not limited to, PEG-bis-chlorosulfone and PEG-bis-vinylsulfone (see WO 95/13312).

WO 97/04003, the disclosure of which is hereby incorporated by reference for any purpose, teaches methods of making sulfone-activated linkers by obtaining a compound having a reactive hydroxyl group and converting the hydroxyl group to a reactive Michael acceptor to form an activated linker, with tetrahydrofuran as the solvent for the conversion. The application also teaches a process for purifying the activated linkers, which utilizes hydrophobic interaction chromatography to separate the linkers based on size and end-group functionality.

As an example, chemically modified derivatives of a molecule may provide such advantages as increased stability, increased time in circulation, or decreased immunogenicity (see, e.g., U.S. Pat. No. 4,179,337). The chemical moieties for derivitization may be selected from water-soluble polymers such as, but are not limited to, polyethylene glycol, ethylene glyco/propylene glycol copolymers, carboxymethylcellulose, dextran, polyvinyl alcohol and the like. According to certain embodiments, the polypeptides may be modified at random positions within the molecule, or at predetermined positions within the molecule and may include one, two, three or more attached chemical moieties.

In certain embodiments, one may specifically desire N-terminally chemically modified protein. Using polyethylene glycol as an illustration of the present compositions, in certain embodiments, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. In certain embodiments, the method of obtaining the N-terminally pegylated preparation (i.e., separating this moiety from other monopegylated moieties if necessary) may be by purification of the N-terminally pegylated material from a population of pegylated protein molecules. In certain embodiments, selective N-terminal chemical modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Polyvalent Forms

Techniques for formation of polyvalent forms include, but are not limited to, photochemical crosslinking (e.g., exposure to ultraviolet light), chemical crosslinking (e.g., with bifunctional linker molecules such as polyethylene glycol), and mutagenesis (e.g., introduction of additional cysteine residues).

Polyvalent forms may be constructed by chemically coupling at least one parent molecule and another moiety with any clinically accepted linker (e.g., a water-soluble polymer). In principle, the linker typically should not impart new immunogenicity. In certain embodiments, the linker also typically should not, by virtue of the new amino acid residues, alter the hydrophobicity and charge balance of the structure, which affects its biodistribution and clearance. A variety of chemical crosslinkers may be used depending upon which properties of the protein dimer are desired. For example, in certain embodiments, crosslinkers may be short and relatively rigid or longer and more flexible, may be biologically reversible, and may provide reduced immunogenicity or longer pharmacokinetic half-life.

In certain embodiments, molecules are linked through the amino terminus by a two-step synthesis. In the first step, one molecule is chemically modified at the amino terminus to introduce a protected thiol, which after purification is deprotected and used as a point of attachment for site-specific conjugation through a variety of crosslinkers with a second molecule. Amino-terminal crosslinks include, but are not limited to, a disulfide bond, thioether linkages using short-chain, bis-functional aliphatic crosslinkers, and thioether linkages to variable length, bifunctional polyethylene glycol crosslinkers (PEG "dumbbells"). Also encompassed by PEG dumbbell synthesis of dimers is a byproduct of such synthesis, termed a "monobell." A monobell includes, but is not limited to, a monomer coupled to a linear bifunctional PEG with a free polymer terminus. Alternatively, in certain embodiments, molecules may be crosslinked directly through a variety of amine specific homobifunctional crosslinking techniques which include reagents such as, but not limited to,: diethylenetriaminepentaacetic dianhydride (DTPA), p-benzoquinone (pBQ), or bis(sulfosuccinimidyl) suberate ($BS^3$) as well as others known in the art. In certain embodiments, it is also possible to thiolate a molecule directly with reagents such as iminothiolane in the presence of a variety of bifunctional, thiol specific crosslinkers, such as PEG bismaleimide, and achieve dimerization and/or dumbbells in a one step process.

In certain embodiments, the water-soluble polymers for this polyvalent form can be, based on the monomers listed herein, homopolymers, random or block copolymers, terpolymers straight chain or branched, substituted or unsubstituted. The polymer can be of any length or molecular weight, but these characteristics can affect the biological properties. Polymer average molecular weights particularly useful for decreasing clearance rates in pharmaceutical applications typically are in the range of 2,000 to 35,000 daltons. In addition, in certain embodiments, the length of the polymer can be varied to optimize or confer the desired biological activity.

In certain embodiments, a bivalent molecule may include two tandem repeats of parent molecules separated by a polypeptide linker region. The design of the polypeptide linkers can be similar in design to the insertion of short loop sequences between domains in the de novo design of proteins (Mutter (1988), *TIBS,* 13:260–265 and Regan and DeGrado (1988), *Science,* 241:976–978, the disclosures of which are hereby incorporated by reference for any purpose). Several different linker constructs have been assembled and shown to be useful for forming single chain antibodies; the most functional linkers typically vary in size from 12 to 25 amino acids (amino acids having unreactive side groups, e.g., alanine, serine and glycine) which together constitute a hydrophilic sequence, have a few oppositely charged residues to enhance solubility and are flexible (Whitlow and Filpula (1991), *Methods: A Companion to Methods in Enzymology,* 2:97–105; and Brigido et al. (1993), *J. Immunol.,* 150:469–479, the disclosures of which are hereby incorporated by reference for any purpose). It has been shown that a linker suitable for single chain antibodies is effective to produce a dimeric form of the human sTNFR-II (Neve et al. (1996), *Cytokine,* 8(5):365–370, the disclosure of which is hereby incorporated by reference for any purpose).

In certain embodiments, polyvalent forms may also be formed using substitution variants. In certain embodiments, parent molecules may be modified to form dimers or multimers by site-directed mutagenesis to create unpaired cysteine residues for interchain disulfide bond formation.

Additionally, in certain embodiments, a parent molecule may be chemically coupled to biotin, and the resulting conjugate may then be allowed to bind to avidin, resulting in tetravalent avidin/biotin/parent molecules. In certain embodiments, parent molecule may also be covalently coupled to dinitrophenol (DNP) or trinitrophenol (TNP) and the resulting conjugates precipitated with anti-DNP or anti-TNP-IgM to form decameric conjugates.

In certain embodiments, recombinant fusion proteins may also be produced wherein each recombinant chimeric molecule has a parent molecule(s) sequence amino-terminally or carboxy-terminally fused to all or part of the constant domains, but to at least one constant domain, of the heavy or light chain of human immunoglobulin. In certain embodiments, following transcription and translation of a heavy-chain chimeric gene, or of a light chain-containing gene and a heavy-chain chimeric gene, the gene products may be assembled into a single chimeric molecule having a parent molecule(s) displayed bivalently. Additional details relating to the construction of such chimeric molecules are disclosed, e.g., in U.S. Pat. No. 5,116,964, WO 89/09622, WO 91/16437, WO 97/23614 and EP 315062, the disclosures of which are hereby incorporated by reference for any purpose.

Pharmaceutical Compositions

Unless otherwise noted, all statements concerning pharmaceutical compositions in this specification refer to compositions comprising IL-1 inhibitor, an EPO receptor agonist, a TNF-α inhibitor or a combination of EPO receptor agonist and IL-1 inhibitor and/or TNF-α inhibitor.

In certain embodiments, the invention provides for pharmaceutical compositions comprising a pharmaceutically acceptable diluent, carrier, solubilizer, emulsifier, preservative and/or adjuvant. In certain embodiments, the therapeutic molecules can be formulated together or packaged together in a kit. In certain embodiments, the composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Also encompassed, in certain embodiments, are compositions comprising any of the therapeutic molecules modified with water-soluble polymers to increase solubility or stability. In certain embodiments, compositions may also comprise incorporation of any of the therapeutic molecules into liposomes, microemulsions, micelles or vesicles for controlled delivery over an extended period of time.

Specifically, in certain embodiments, compositions herein may comprise incorporation into polymer matrices such as hydrogels, silicones, polyethylenes, ethylene-vinyl acetate copolymers, or biodegradable polymers. Examples of hydrogels include, but are not limited to, polyhydroxyalkylmethacrylates (p-HEMA), polyacrylamide, polymethacrylamide, polyvinylpyrrolidone, polyvinyl alcohol and various polyelectrolyte complexes. Examples of biodegradable polymers include, but are not limited to, polylactic acid (PLA), polyglycolic acid (PGA), copolymers of PLA and PGA, polyamides and copolymers of polyamides and polyesters. Other controlled release formulations include, but are not limited to, microcapsules, microspheres, macromolecular complexes and polymeric beads which may be administered by injection.

Selection of a particular composition will depend upon a number of factors, including, but not limited to, the condition being treated, the route of administration, and the pharmacokinetic parameters desired. A more extensive survey of component suitable for pharmaceutical compositions is found in *Remington's Pharmaceutical Sciences,* 18th ed. A. R. Gennaro, ed. Mack, Easton, Pa. (1980), which is hereby incorporated by reference for any purpose.

In certain embodiments, an effective amount or amounts of the therapeutic molecules will depend, for example, upon the therapeutic objectives, the route of administration, and the condition of the patient. Accordingly, in certain embodiments, the therapist may titer the dosage and modify the route of administration as needed to obtain the optimal therapeutic effect. A typical daily dosage may range from about 0.1 mg/kg to up to 100 mg/kg or more, depending on the factors mentioned above. In certain embodiments, a clinician can administer the composition or compositions until a dosage is reached that achieves the desired increase in hematocrit or clinical improvement of the blood disorder.

In certain embodiments, the composition or compositions may be administered as a single dose, or as two or more doses of one or more of the therapeutic molecules. These doses can consist of the same or different amounts of the therapeutic molecules and can be administered at the same or different times via the same or different routes of administration. In certain embodiments, the composition may be administered as a composition comprising any one or any combination of the therapeutic molecules. In certain embodiments, the combination may include the same or different amounts of the therapeutic molecules. In certain embodiments, the composition or compositions may be administered as a continuous infusion via implantation device or catheter. In embodiments in which the continuous infusion contains more than one therapeutic molecule, it may contain the same or different concentrations of the therapeutic molecules.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The compositions to be used for in vivo administration typically are sterile. In certain embodiments, this can be readily accomplished by filtration through sterile filtration membranes. Where the compositions are lyophilized, sterilization using these methods may be conducted either prior to, or following, lyophilization and reconstitution. In certain embodiments, the compositions for parenteral administration may be stored in lyophilized form or in solution.

In certain embodiments, compositions can be placed into a container having a sterile access port, for example, an intravenous solution bag or vial having a stopper pierceable by a hypodermic injection needle.

The route of administration of the compositions are in accord with known methods including, but not limited to, oral, nasal, pulmonary, rectal administration or injection or infusion by subcutaneous, intravenous, intraperitoneal, intracerebral (intraparenchymal), intracerebroventricular, intramuscular, intraocular, intraarterial, or intralesional routes, or by sustained release systems or implantation device which may optionally involve the use of a catheter. In certain embodiments, the compositions may be administered continuously by infusion, bolus injection or by implantation device.

In certain embodiments, compositions may be administered locally via implantation into the affected area of a membrane, sponge, or other appropriate material on to which the therapeutic molecule or molecules have been absorbed. In certain embodiments, where an implantation device is used, the device may be implanted into any suitable tissue or organ, and delivery of the compositions may be directly through the device via bolus, or via continuous administration, or via catheter using continuous infusion.

In certain embodiments, compositions may be administered in a sustained release formulation or preparation. Suitable examples of sustained-release preparations include, but are not limited to, semipermeable polymer matrices in the form of shaped articles, e.g. films, or microcapsules. Sustained release matrices include, but are not limited to, polyesters, hydrogels, polylactides (U.S. Pat. No. 3,773,919, EP 58,481), copolymers of L-glutamic acid and gamma ethyl-L-glutamate (Sidman et al, Biopolymers, 22: 547–556 [1983]), poly (2-hydroxyethyl-methacrylate) (Langer et al., J. Biomed. Mater. Res., 15: 167–277 [1981] and Langer, Chem. Tech., 12: 98–105 [1982]), ethylene vinyl acetate (Langer et al., supra) or poly-D(-)-3-hydroxybutyric acid (EP 133,988). Sustained-release compositions also may include, but are not limited to, liposomes, which can be prepared by any of several methods known in the art (e.g., Eppstein et al., Proc. Natl. Acad. Sci. USA, 82: 3688–3692 [1985]; EP 36,676; EP 88,046; EP 143,949).

In certain embodiments, it may be desirable to use compositions in an ex vivo manner. Here, cells, tissues, or organs that have been removed from the patient are exposed to compositions after which the cells, tissues and/or organs are subsequently implanted back into the patient.

In certain embodiments, compositions may be delivered through implanting into patients certain cells that have been genetically engineered, using methods known in the art, to express and secrete the polypeptides, fragments, variants, or derivatives. In certain embodiments, such cells may be animal or human cells, and may be derived from the patient's own tissue or from another source, either human or non-human. In certain embodiments, the cells may be immortalized. However, in order to decrease the chance of an immunological response, in certain embodiments, the cells can be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and U.S. Pat. No. 5,106,627. A system for encapsulating living cells is described in PCT WO 91/10425 (Aebischer et al.). Techniques for formulating a variety of other sustained or controlled delivery products, such as liposome carriers, bio-erodible particles or beads, are also known to those in the art, and are described, for example, in U.S. Pat. No. 5,653,975 (Baetge et al., CytoTherapeutics, Inc.). In certain embodiments, the cells, with or without encapsulation, may be implanted into suitable body tissues or organs of the patient.

When administered parenterally, proteins may be cleared rapidly from the circulation and may therefore elicit relatively short-lived pharmacological activity. Consequently, frequent injections of relatively large doses of bioactive proteins may be used to sustain therapeutic efficacy with this method of administration. Proteins modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified proteins [Abuchowski et al., In: "Enzymes as Drugs", Holcenberg et al., eds. Wiley-Interscience, New York, N.Y., 367–383 (1981), Newmark et al., J. Appl. Biochem. 4:185–189 (1982), and Katre et al., Proc. Natl. Acad. Sci. USA 84, 1487–1491 (1987), incorporated by reference for any purpose]. Such modifications may also increase the protein's solubility in aqueous solution, eliminate or decrease aggregation, enhance the physical and chemical stability of the protein, and greatly reduce the immunogenicity and antigenicity of the protein. As a result, in certain embodiments, the desired in vivo biological activity may be achieved by the administration of such polymer-protein adducts less frequently or in lower doses than with the unmodified protein. In certain embodiments, IL-1 inhibitors and/or TNF inhibitors can be used alone or with one or more additional hematopoietic factors or other therapeutic molecules, such as EPO (Epogen®), novel erythropoiesis stimulating protein (NESP, Aranesp™), G-CSF (Neupogen®) and derivatives thereof, GM-CSF, CSF-1, IL-2, IL-3, IL-4, IL-5, IL-6, IL-7, IL-8, IL-9, IL-10, IL-11, IL-18BP, IL-18 inhibitor (e.g., IL-18 antibody), interferon gamma (IFN-γ) inhibitor (e.g., IFN-γ antibody), IGF-1, or LIF (Leukemic Inhibitory Factor) in the treatment of hematopoietic disorders.

There are many diseases which may be treatable with IL-1 and/or TNF inhibitors or such inhibitors and EPO receptor agonists in certain embodiments. These include, but are not limited to, the following: myelofibrosis, myelosclerosis, osteopetrosis, metastatic carcinoma, acute leukemia, multiple myeloma, Hodgkin's disease, lymphoma, Gaucher's disease, Niemann-Pick disease, Letterer-Siwe disease, refractory erythroblastic anemia, Di Guglielmo syndrome, congestive splenomegaly, Hodgkin's disease, Kala azar, sarcoidosis, primary splenic pancytopenia, miliary tuberculosis, disseminated fungus disease, fulminant septicemia, malaria, vitamin B12 and folic acid deficiency, pyridoxine deficiency, Diamond Blackfan anemia, hypopigmentation disorders such as piebaldism and vitiligo.

In certain embodiments, treatment with an IL-1 and/or TNF inhibitor or such inhibitors and an EPO receptor agonist may also be used for enhancing hematopoietic recovery after acute blood loss.

Assays

To test for suitable compounds for treatment to increase the hematocrit level, any assays or in vivo protocols that test for such activity may be employed. Examples of such assays and in vivo protocols are included in international patent application WO 00/24893, hereby incorporated for reference for any purpose. Those skilled in the art will be familiar with suitable assays.

The following examples are offered to illustrate more fully the invention, but are not construed as limiting the scope thereof.

EXAMPLE 1

Administration of an IL-1ra Analog Increases Hematocrit Levels

In a multi-center, double-blind, dose-ranging study, subjects with active severe or very severe rheumatoid arthritis (N=472) received daily subcutaneous injections for 6 months of placebo, 30, 75, or 150 mg of a recombinant, non-glycosylated IL-1ra analog ("anakinra"). See FIG. 1 for baseline demographics and disease history by treatment group. Anakinra is a non-glycosylated form of human IL-1ra that is recombinantly made in *E. coli*.

Anakinra was injected at concentrations of either 30, 75, or 150 mg/ml of purified anakinra in suspending solution. The suspending solution contained 140 mM sodium chloride, 10 mM sodium citrate, 0.1% (w/w) polysorbate 80, 0.5 mM EDTA, and sterile water for injection. Placebo consisted of the suspending solution. Anakinra and placebo solutions were stored at temperatures between 20 and 80° C. The pH of all solutions was 6.5.

A total volume of 1 ml was injected each day. Possible sites of injection included, but were not limited to, the front of the thigh, the abdomen above the navel, and the back of the upper arm. It was recommended that subjects rotate the site of injection. Subjects were instructed to inject the study solution at the same time of the day for all 24 weeks, preferably in the evening.

Hematocrit was assessed at baseline and after 24 weeks of the anakinra therapy. The difference in change from baseline at week 24 in hematocrit (volume percentages) between the pooled anakinra group and the placebo group was assessed via the Wilcoxon-Mann-Whitney test (E. L. Lehmann, *Nonparametrics: Statistical Methods Based on Ranks*, 1975, hereby incorporated by reference for any purpose) and confirmed with a two sample t-test.

The mean hematocrit of subjects treated with anakinra increased by 0.28 volume-percentages over six months, whereas the mean hematocrit of subjects treated with placebo decreased by 0.867 volume-percentages over the same time period (FIG. 2).

EXAMPLE 2

Administration of Anakinra Improves Anemia

In the study of the effect of anakinra on hematocrit levels described in Example 1, a subset of subjects with rheumatoid arthritis were anemic, as defined as hematocrit level less than or equal to thirty-four percent (Pincus et al., Am. J. Med 89:161, 1990, which is incorporated by reference for any purpose), upon initiation of the study. Fifty (14.2%) of the anakinra-treated subjects and thirteen (10.7%) of the placebo-treated subjects were characterized with this degree of anemia (see FIG. 3 for baseline demographics and disease history).

Although the number of anemic subjects in this study was small, more patients treated with anakinra exhibited improvement in hematocrit levels after twenty-four weeks of treatment than did subjects receiving the placebo. Anemia improved in patients taking each of the three doses of IL-1ra (see FIG. 4 for results).

EXAMPLE 3

Administration of Anakinra May Improve Anemia Independently of Articular Disease In the study of the effect of the administration of anakinra on anemia described in Example 2, three of the seven anakinra-treated patients with greater than or equal to six volume-percentage improvement in hematocrit levels did not meet the ACR20 response criteria (FIGS. 5 and 6). The ACR20 defines a subject as improved if the following criteria are met:>20% decrease from baseline in the number of tender/painful joints; >20% decrease from baseline in the number of swollen joints; and >20% decrease from baseline in 3 of the following 5 criteria: 1) subject assessment of disease activity; 2) investigator assessment of disease activity; 3) subject assessment of pain; 4) disability score from the Health Assessment Questionnaire (HAQ); or 5) C-reactive protein. Thus, IL-1ra therapy may improve anemia in rheumatoid arthritis subjects independently of its effect on articular disease activity.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

EXAMPLE 4

On day 0, a group of eight to ten week old female Lewis rats were immunized with an intraperitoneal (i.p.) injection of peptidoglycan-polysaccharide polymers (PG-APS) (Lee Laboratories, Grayson, Ga.) equilibrated to a dose of 15 µg rhamose/kg in 0.85% saline (3 mg/rat in a volume of 0.520 ml, rats injected with stock PG-APS). Also, on day 0, another group of eight to ten week old female Lewis rats received 0.5 ml i.p. injections of 0.85% saline to make carrier-injected rats.

From day 0 to day 77, blood was collected weekly from tail arteries into EDTA-coated Microtainer tubes (Becton Dickinson, Franklin Lakes, N.Y.) and complete blood counts (CBC) were performed on an ADVIA 120 Hematology System (Bayer Corporation, Tarrytown, N.Y.) calibrated for rat blood. On day 42, the rats were divided into two groups. Rats with mean hemoglobin (Hb) concentrations below 12.0 g/dL were termed anemic. Anemic rats that possessed similar mean Hb concentrations were placed in the experimental group.

The control group consisted of carrier-injected rats that possessed similar Hb concentrations to each other.

Beginning on day 43, rats in the experimental group were subdivided into eight treatment groups. All groups were n=5 except the carrier group, which had an n=6. Seven groups were treated with one of the following treatment regimens: a) 100 mg/kg of Fc-IL-1ra three times per week, b) 3 μg/kg of ARANESP™ once every two weeks c) 6 μg/kg of ARANESP™ once every two weeks, d) 100 mg/kg of Fc-IL-1ra three times per week and 3 μg/kg of ARANESP™ once every two weeks, or e) 100 mg/kg of Fc-IL-1ra three times per week and 6 μg/kg of ARANESP™ once every two weeks f) 4 mg/kg of PEG sTNR-R1 three times per week g) 4 mg/kg of PEG sTNR-R1 three times per week and 3 μg/kg of ARANESP™ once every two weeks h) 4 mg/kg of PEG sTNR-R1 three times per week and 6 μg/kg of ARANESP™ once every two weeks. One group of the experimental rats was injected with 0.4 mL carrier solution on the same schedule as the cytokine inhibitors and were housed and bled the same as all the experimental groups. The treatment period lasted until day 57.

Experimental data was obtained blood drawn from tail vein and analyzed on the ADVIA complete blood count (CBC) analysis machine (Bayer, Inc) the same day of sampling and according the manufacture's protocol. Blood for serum was collected into centrifugal serum separator devices, allowed to clot, spun at 3000 rpm for 5 minutes, serum was pipetted off and put into Eppendorf tubes, stored in −80 until delivery to LabCorp, Inc. (Research Park, N.C.). via overnight courier on dry ice. Blood collected for CBC occurred on days 30, 42, 45, 49, 52, 56, 59, 63, 66, 70, 77. Blood collected for serum occurred on days 0, 42, 49, 57, 63, 77. In summary, after therapeutic treatment began, rats were bled twice a week for CBC analysis and once a week for serum].

All of these parameters, except iron concentrations, are part of the data generated by the "complete blood count" (CBC) analysis which are produced simultaneously by the Advia machine analysis already described above. Total serum Iron concentrations (TSI) and transferrin total iron binding capacity were measured by LabCorp, Inc. (Research Park, N.C.). Unsaturated iron binding capacity (UIBC) was calculated as follows: TIBC−TSI=UIBC. (See: "Clinical Biochemistry of Domestic Animals" pages 263–264. Jiro J. Kaneko, Ed., Academic Press Inc. Harcourt Brace Jovanovich Publishers). Paw volume was determined as described in Feige U, et al., Cellular Molecular Life Sciences 57:1457–1470 (2000).

Rats from the experimental group treated with Fc-IL-1ra alone trended toward higher mean serum Hb concentrations and reduced mean paw edema compared to untreated rats from the experimental group. Administration of 100 mg/kg Fc-IL-1ra increased mean serum Hb concentrations by 1.8 g/dL over the mean serum Hb concentrations of untreated rats (p=0.1) (see FIG. 7) and reduced mean paw volumes by 0.4 ml relative to the mean paw volumes of untreated rats (p=0.1) (see FIG. 8). Rats from the experimental group treated with ARANESP™ alone at 3 or 6 μg/kg exhibited elevated mean serum Hb concentrations compared to untreated rats. Treatment with 3 μg/kg ARANESP™ alone increased mean serum Hb concentrations by 0.4 g/dL over the mean serum Hb concentrations of untreated rats (p=0.7) (see FIG. 7). Treatment with 6 μg/kg ARANESP™ alone increased mean serum Hb concentrations by 1.3 g/dL over the mean serum Hb concentrations of untreated rats (p=0.4) (see FIG. 7).

Treatment of rats from the experimental group with 100 mg/kg Fc-IL-1ra and 3 μg/kg ARANESP™ did not significantly increase mean serum Hb concentrations compared to treatment by 100 mg/kg Fc-IL-1ra alone. However, treatment of rats from the experimental group with 100 mg/kg Fc-IL-1ra and 6 μg/kg ARANESP™ more than doubled the increase in mean serum Hb concentrations compared to treatment with Fc-IL-1ra or ARANESP™ alone. Treatment with 100 mg/kg Fc-IL-1ra and 6 μg/kg ARANESP™ increased mean serum Hb concentrations by 2.2 g/dL more than the increase from treatment with 100 mg/kg Fc-II-1ra alone (p=0.04) (see FIG. 7). Treatment with 100 mg/kg Fc-IL-1ra and 6 μg/kg ARANESP™ increased mean serum Hb concentrations by 2.7 g/dL more than the increase from treatment with 6 μg/kg ARANESP™ alone (p=0.01) (see FIG. 7). Thus, the total increase rats in mean serum Hb concentrations over untreated experimental rats resulting from treatment with 100 mg/kg Fc-IL-1ra and 6 μg/kg ARANESP™ was 4.0 g/dL. This is greater than the sum of the increases in mean serum Hb concentrations over untreated experimental rats resulting from treatment with 100 mg/kg Fc-IL-1ra alone (1.8 g/dL) and 6 μg/kg ARANESP™ alone (1.3 g/dL).

Figure 9:
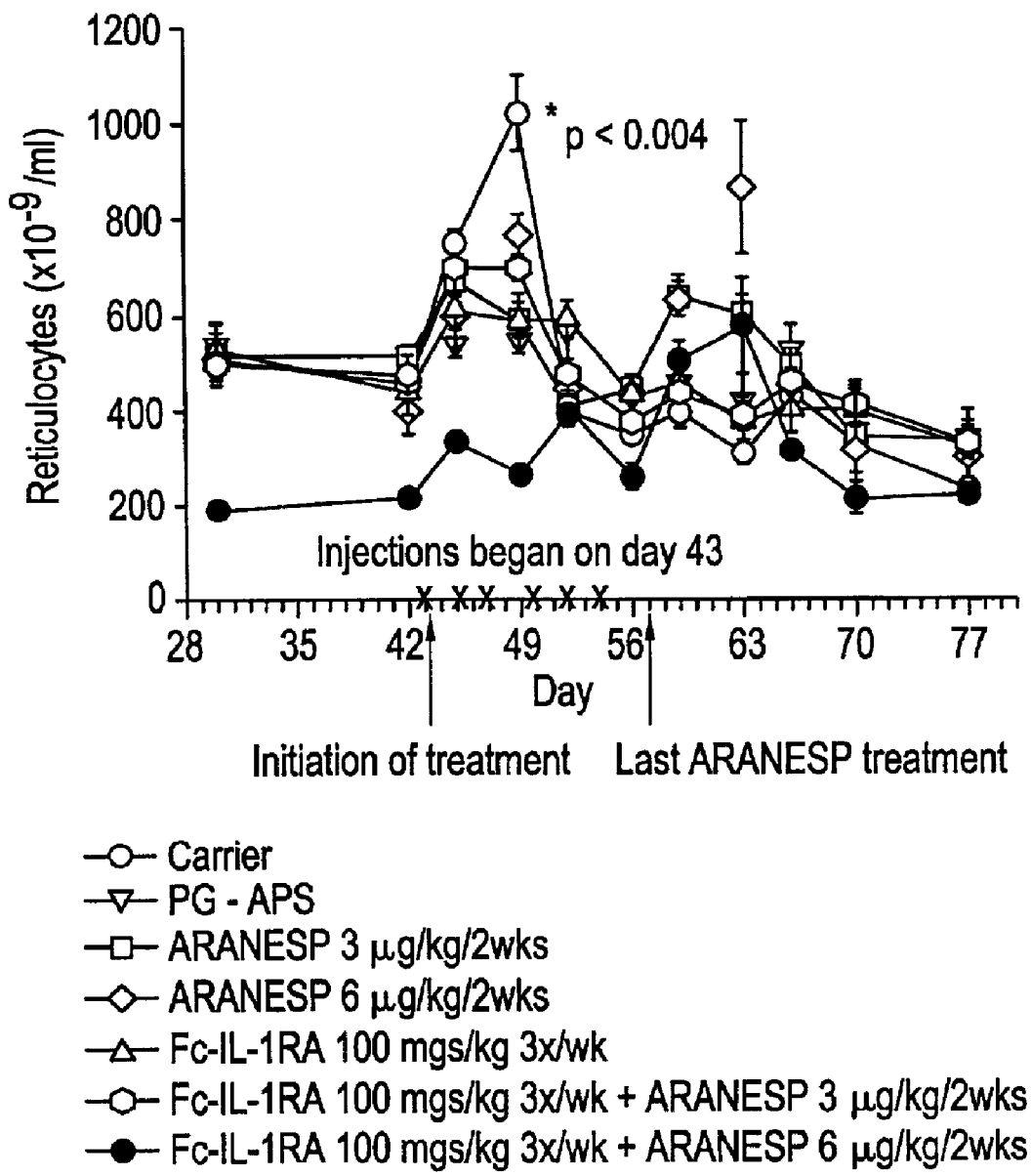
FIG. 9 shows the effect of ARANESP™ and Fc-IL-1ra on mean reticulocyte numbers in rats afflicted with anemia of chronic disorders in the study described in Example 4 of this application. Combination treatment of Fc-IL-1RA 100 mgs/kg 3×/wk with ARANESP 6 μg/kg/2wks was significantly better at raising reticulocyte levels than either single treatment alone (p<0.004).
Figure 10:
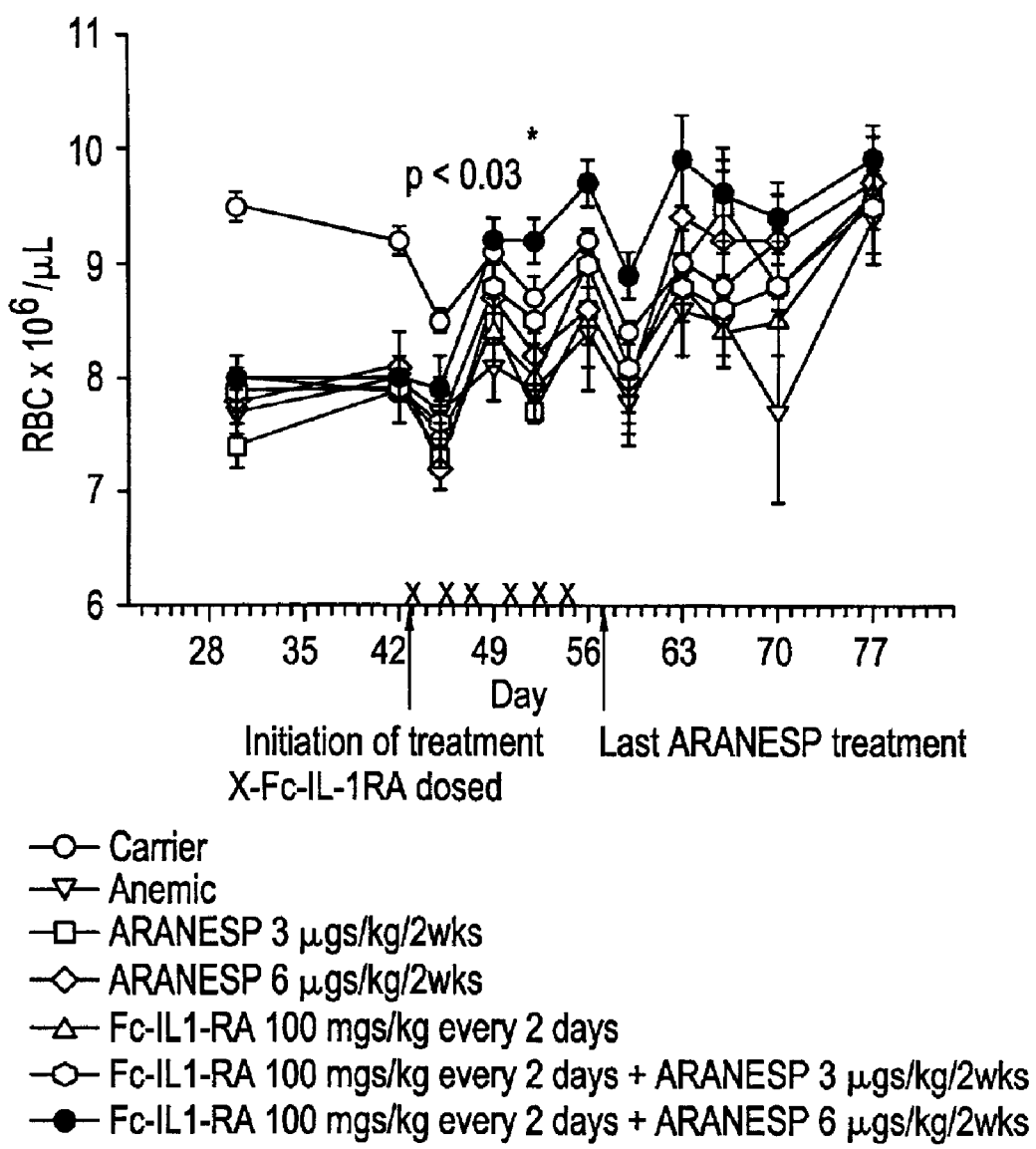
FIG. 10 shows the effect of ARANESP™ and Fc-IL-1ra on red blood cell (RBC) numbers in rats afflicted with anemia of chronic disorders in the study described in Example 4 of this application. Treatment of rats from the experimental group with 100 mg/kg Fc-IL-1ra and 6μg/kg ARANESP™ increased red blood cell (RBC) numbers (p<0.03) compared to the same dose of 6 μg/kg ARANESP™ alone. Combination treatment of Fc-IL-1RA 100 mgs/kg 3×/wk with ARANESP 6 μg/kg/2wks was significantly better at raising RBC numbers than either single treatment alone (p<0.03).
Figure 11:
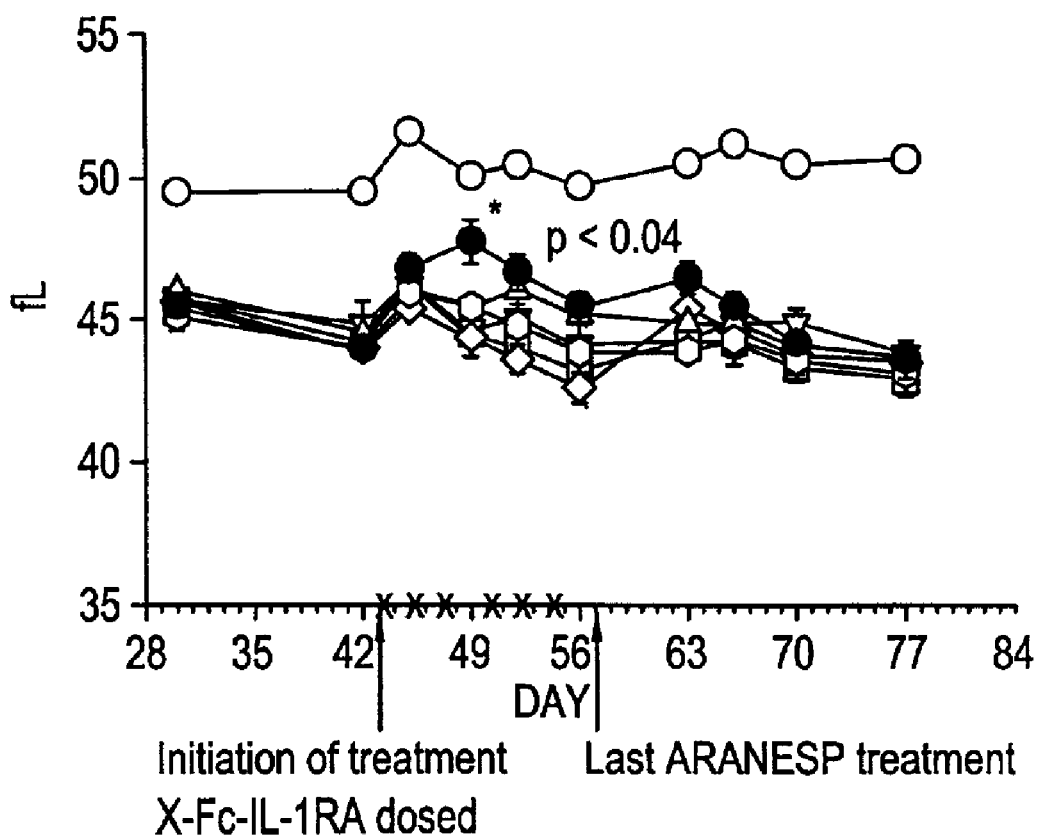
FIG. 11 shows the effect of ARANESP™ and Fc-IL-1ra on mean corpuscular volume (MCV) in rats afflicted with anemia of chronic disorders in the study described in Example 4 of this application. Combination treatment of Fc-IL-1RA 100 mgs/kg 3×/wk with ARANESP 6 μg/kg/2wks was significantly better at raising MCV than either single treatment alone (p<0.04)
Figure 12:
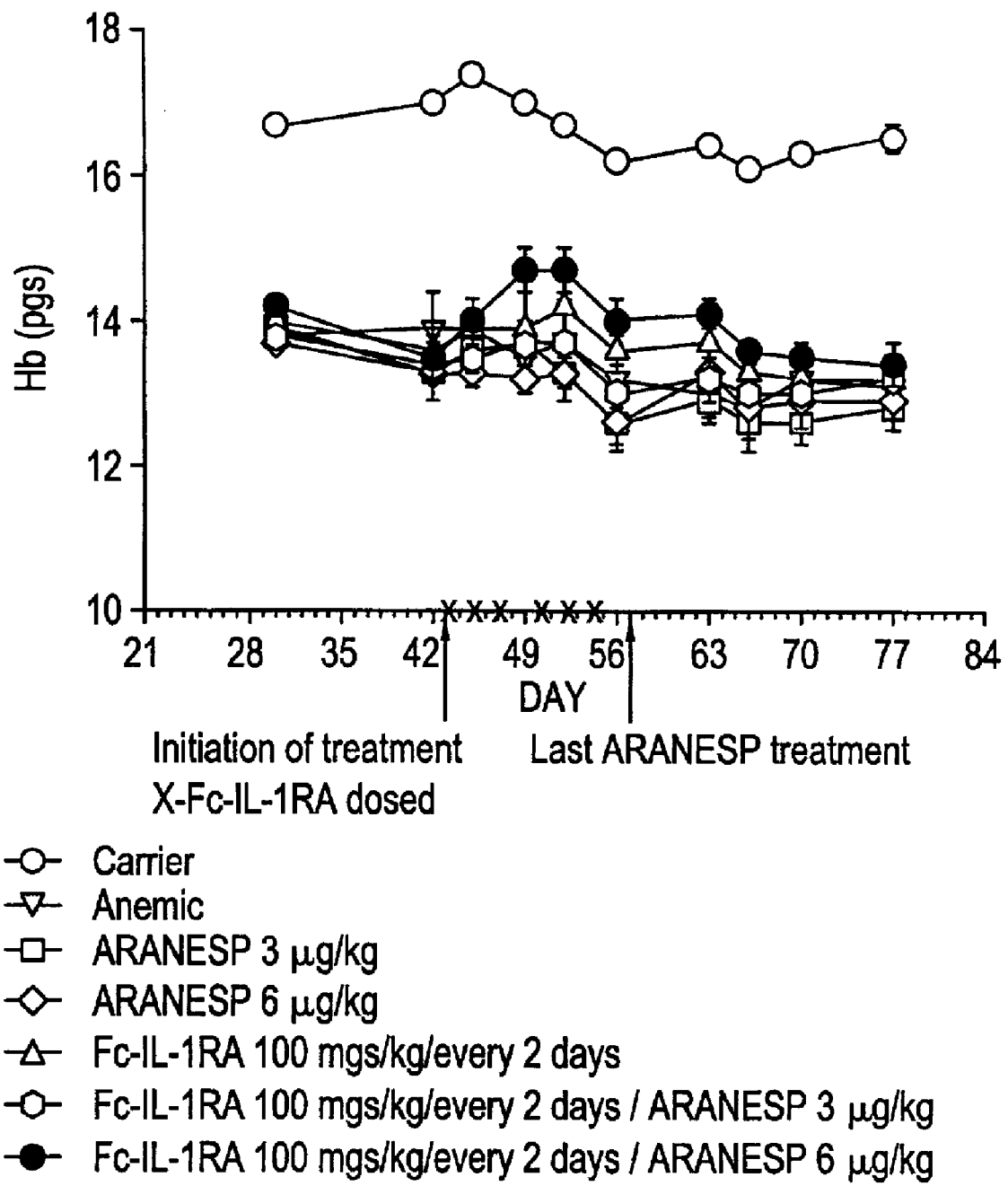
FIG. 12 shows the effect of ARANESP™ and Fc-IL-1ra on mean corpuscular hemoglobin (MCH) in rats afflicted with anemia of chronic disorders in the study described in Example 4 of this application. Combination treatment of Fc-IL-1RA 100 mgs/kg 3×/wk with ARANESP 6 μg/kg/2wks was significantly better at raising MCV than ARANESP treatment alone (p<0.01).
Figure 13:
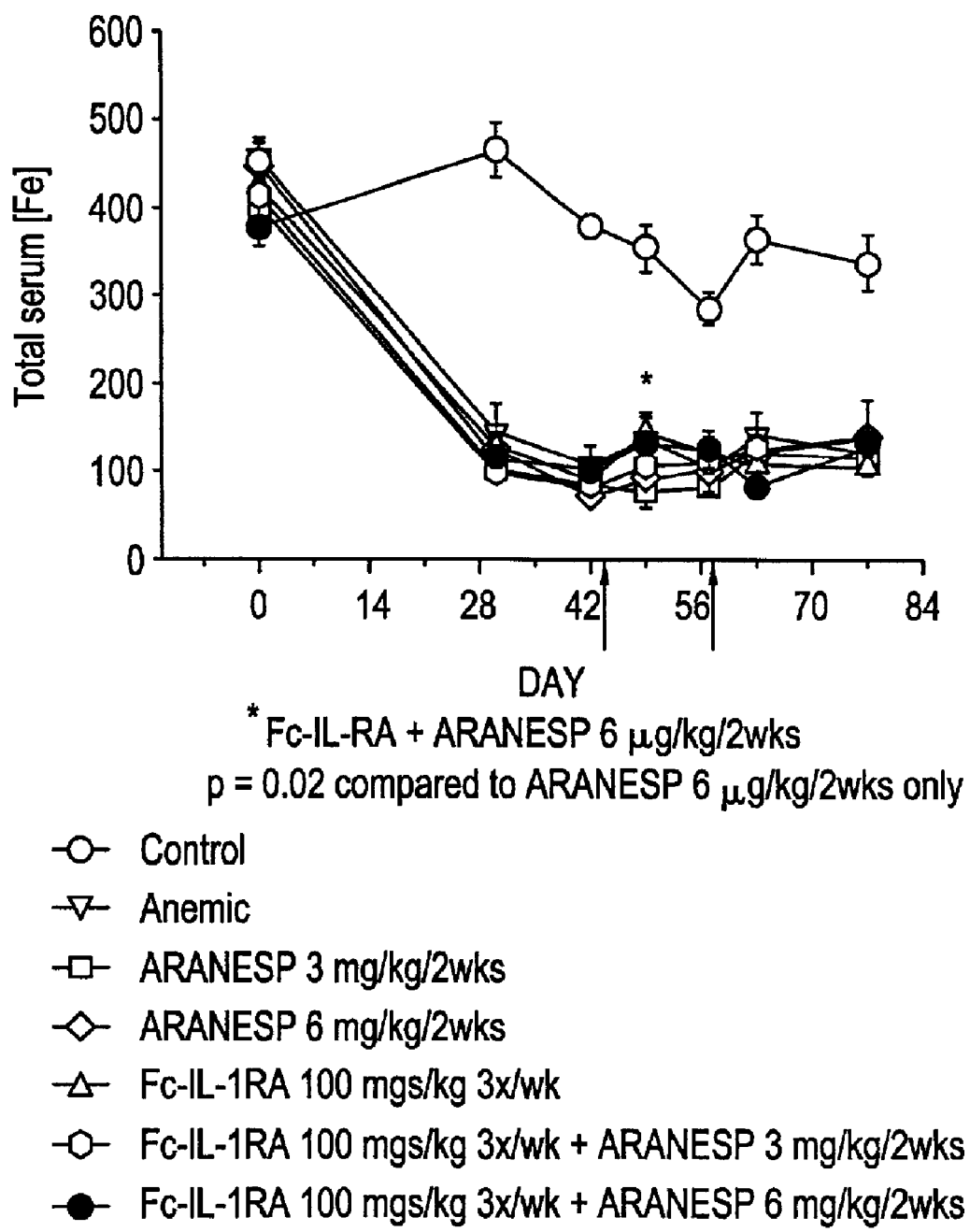
FIG. 13 shows the effect of ARANESP™ and Fc-IL-1ra on total serum iron concentrations (TSI) in rats afflicted with anemia of chronic disorders in the study described in Example 4 of this application. Combination treatment of Fc-IL-1RA 100 mgs/kg 3×/wk with ARANESP 6 μg/kg/2wks was significantly better at raising TSI than either single treatment alone (p<0.02).
Figure 14:
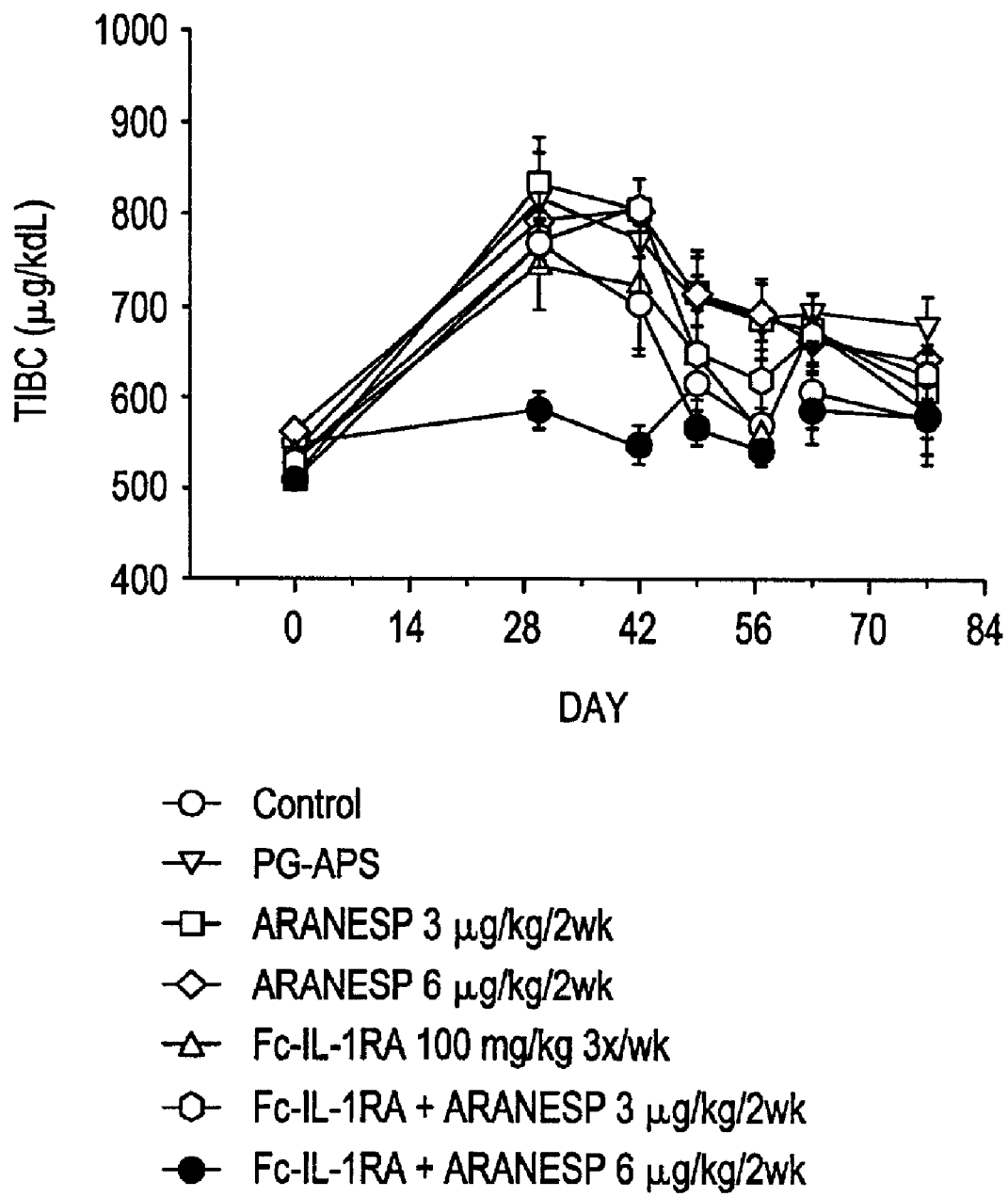
FIG. 14 shows the effect of ARANESP™ and Fc-IL-1ra on total iron binding capacity (TIBC) in rats afflicted with anemia of chronic disorders in the study described in Example 4 of this application.
Figure 15:
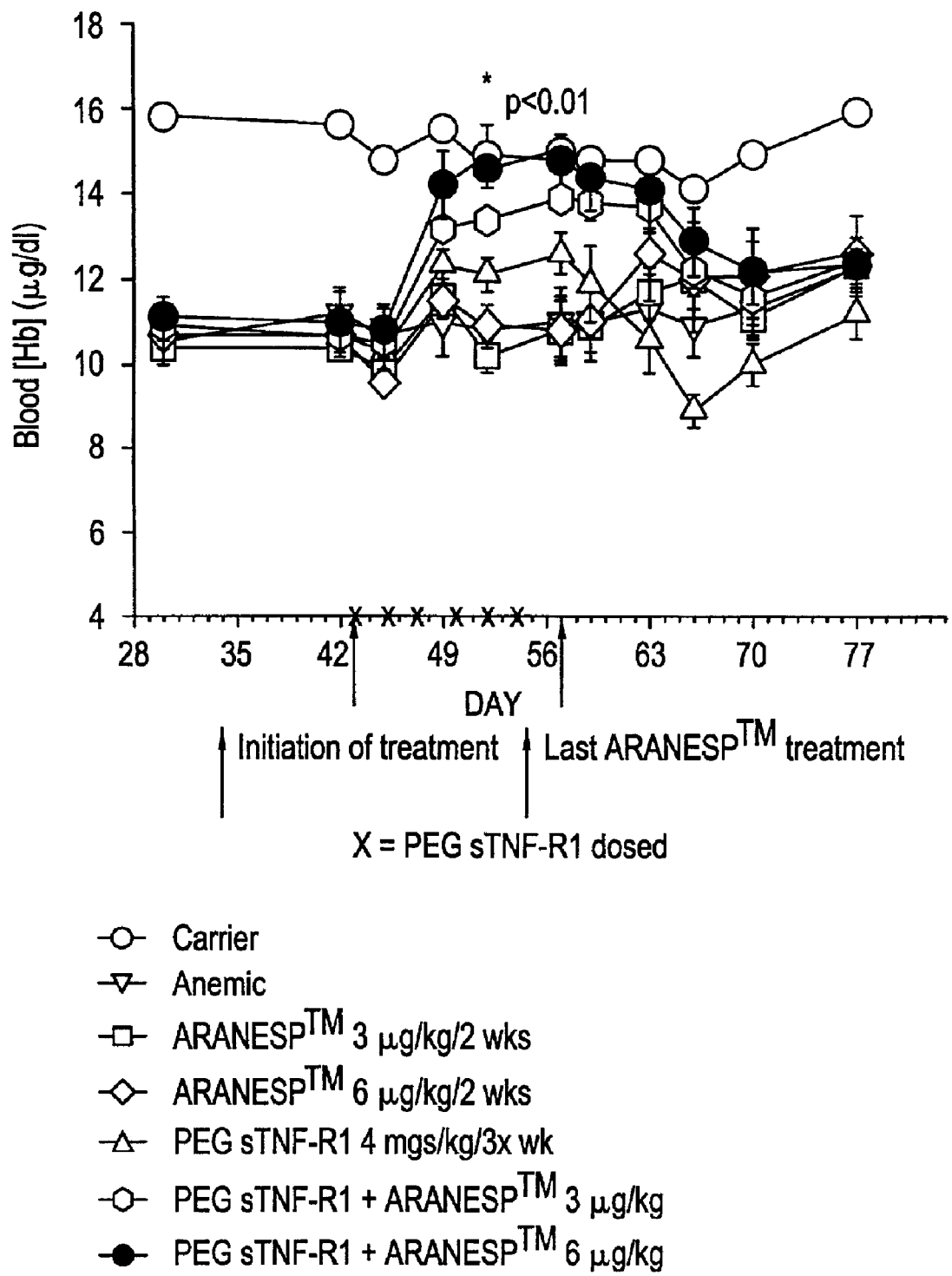
FIG. 15 shows the effect of ARANESP™ and PEG sTNF R1 on mean blood hemoglobin concentration in rats afflicted with anemia of chronic disorders in the study described in Example 4 of this application. Combination treatment of PEG sTNF R1 at 4 mgs/kg 3×/wk with ARANESP 6 μg/kg/2wks was significantly better at raising blood Hb levels than either single treatment alone (p<0.01)

Treatment of rats from the experimental group with both 100 mg/kg Fc-IL-1ra and 6 μg/kg ARANESP™ increased mean reticulocyte numbers (p<0.004) compared to the same dose of either single treatment alone and red blood cell (RBC) numbers (p<0.03) compared to the same dose of 6 μg/kg ARANESP™ alone (see FIGS. 9 and 10). Treatment of rats from the experimental group with both 100 mg/kg Fc-IL-1ra and 6 μg/kg ARANESP™ also increased total serum iron concentrations by 44 μg/dL more than treatment with 6 μg/kg ARANESP™ alone (p=0.02) (see FIG. 14). Treatment with both 100 mg/kg Fc-IL-1ra and 6 μg/kg ARANESP™ also increased mean corpuscular volume to a greater extent than 6 μg/kg ARANESP™ alone (p=0.008) or 100 mg/kg Fc-IL-1ra alone (p=0.04) (see FIG. 11). This treatment also increased mean corpuscular Hb to a greater extent than 6 μg/kg ARANESP™ alone (p=0.03) or 100 mg/kg Fc-IL-1ra alone (p=0.08) (see FIG. 12).

What is claimed is:

1. A method of raising hematocrit in a mammal, comprising administering a therapeutically effective amount of a pharmaceutical composition comprising anakinra.

2. The method of claim 1, wherein the hematocrit target is at least about 30%.

3. The method of claim 1, wherein the pharmaceutical composition comprises at least one of a pharmaceutically acceptable diluent, carrier, solubilizer, emulsifier, preservative, and adjuvant.

4. The method of claim 3, wherein the diluent is a buffer solution of sodium citrate or sodium phosphate.

5. The method of claim 3, wherein the diluent is a buffer solution of sodium citrate.

6. The method of claim 3, wherein the solubilizer is polysorbate 80.

7. The method of claim 3, wherein the pharmaceutical composition comprises a pharmaceutically acceptable diluent and solubilizer.

8. The method of claim 7, wherein the diluent is sodium citrate and the solubilizer is polysorbate 80.

9. The method of claim 1, wherein the mammal has anemia associated with a decline or loss of kidney function.

10. The method of claim 1, wherein the mammal has anemia associated with rheumatoid arthritis.

11. The method of claim 1, wherein the mammal has anemia associated with myelosuppressive therapy.

12. The method of claim 11, wherein the myelosuppressive therapy comprises chemotherapeutic or anti-viral drugs.

13. The method of claim 1, wherein the mammal has anemia associated with excessive blood loss.

14. The method of claim 1, which further comprises administering a therapeutically effective amount of iron.

* * * * *